United States Patent
Dikaiou

(10) Patent No.: US 10,335,613 B2
(45) Date of Patent: Jul. 2, 2019

(54) SYSTEMS, METHODS, AND DEVICES FOR COMMISSIONING AND QUALITY ASSURANCE DATA VALIDATION OF RADIATION THERAPY SYSTEMS

(71) Applicant: Varian Medical Systems International AG, Cham (CH)

(72) Inventor: Aikaterini Dikaiou, Zurich (CH)

(73) Assignee: VARIAN MEDICAL SYSTEMS INTERNATIONAL AG, Cham (CH)

(*) Notice: Subject to any disclaimer, the term of this patent is extended or adjusted under 35 U.S.C. 154(b) by 0 days.

(21) Appl. No.: 15/471,482

(22) Filed: Mar. 28, 2017

(65) Prior Publication Data

US 2018/0280730 A1    Oct. 4, 2018

(51) Int. Cl.
*A61N 5/10*    (2006.01)

(52) U.S. Cl.
CPC ................ *A61N 5/1075* (2013.01)

(58) Field of Classification Search
None
See application file for complete search history.

(56) References Cited

U.S. PATENT DOCUMENTS

| | | | |
|---|---|---|---|
| 7,801,269 B2 | 9/2010 | Cravens et al. | |
| 7,907,987 B2* | 3/2011 | Dempsey | A61B 5/055 250/267 |
| 8,321,179 B2 | 11/2012 | Simon et al. | |
| 8,812,077 B2* | 8/2014 | Dempsey | A61N 5/1045 600/410 |
| 9,415,240 B2* | 8/2016 | Jordan | A61B 6/4035 |
| 9,468,776 B2* | 10/2016 | Fredriksson | A61N 5/1031 |
| 9,555,265 B2* | 1/2017 | Schulte | A61N 5/1039 |
| 2002/0052562 A1* | 5/2002 | Lipman | A61B 5/4824 600/557 |
| 2005/0197564 A1* | 9/2005 | Dempsey | A61B 5/055 600/411 |
| 2006/0017009 A1* | 1/2006 | Rink | G01T 1/04 250/484.5 |

(Continued)

OTHER PUBLICATIONS

International Atomic Energy Agency, Record and Verify Systems for Radiation Treatment of Cancer: Acceptance Testing, Commissioning and Quality Control, Vienna, Austria, 2013, p. 55.*

(Continued)

*Primary Examiner* — Tung S Lau
(74) *Attorney, Agent, or Firm* — Shapiro, Gabor and Rosenberger, PLLC

(57) ABSTRACT

Beam configuration data obtained during the commissioning and/or quality assurance (QA) testing of a radiation therapy device can be validated against other radiation therapy devices within the radiotherapy community. Data and parameters from previously commissioned or QA-tested devices can be compiled and analyzed at a remote module. At the remote module, data and parameters obtained from a radiation therapy device undergoing commissioning or QA testing can be compared to the previously compiled data and/or parameters, to factory data and/or parameters, and/or to predetermined device limits, in order to provide an indication to an end user of potential issues or errors. Warnings, feedback, and/or suggestions can be provided to the end user of the radiation therapy device based on the comparison.

27 Claims, 11 Drawing Sheets

(56) References Cited

U.S. PATENT DOCUMENTS

| | | | | |
|---|---|---|---|---|
| 2007/0020793 | A1* | 1/2007 | Adamovics | A61N 5/1048 438/48 |
| 2007/0106754 | A1* | 5/2007 | Moore | G06F 17/3089 709/217 |
| 2007/0168461 | A1* | 7/2007 | Moore | G06F 17/3089 709/217 |
| 2011/0184283 | A1* | 7/2011 | Rivard | A61N 5/1031 600/436 |

OTHER PUBLICATIONS

Sara Bresciani, A pre-treatment quality assurance survey on 384 patients treated with helical intensity-modulated radiotherapy, 2015, 3 pages.*

J Van Dyk, Has the use of computers in radiation therapy improved the accuracy in radiation dose delivery?, XVII InternationalConferenceontheUseofComputersinRadiationTherapy(ICCR2013), 7 pages.*

Atlas™ software. Datasheet [online]. Sun Nuclear Corporation, 2015 [retrieved on Mar. 28, 2017]. Retrieved from the Internet: <URL: https://www.sunnuclear.com/documents/datasheets/atlas.pdf>.

Beyer, G.P., "Commissioning measurements for photon beam data on three TrueBeam linear accelerators, and comparison with Triology and Clinac 2100 linear accelerators," *Journal of Applied Clinical Medical Physics*, 2013, 14(1).

Chang et al., "Commissioning and dosimetric characteristics of TrueBeam system: Composite data of three TrueBeam machines," *Med. Phys.*, Nov. 2012, 39(11): pp. 6981-7018.

Clivio et al., "Evaluation of the machine performance check application for TrueBeam linac," *Radiation Oncology*, 2015, 10:97.

Das et al., "Accelerator beam data commissioning equipment and procedures: Report of the TG-106 of the Therapy Physics Committee of the AAPM," *Med. Phys.*, Sep. 2008, 35(9): pp. 4186-4215.

Doselab software. Product webpage [online]. Mobius Medical Systems, [retrieved on Mar. 28, 2017]. Retrieved from the Internet: <URL: http://mobiusmed.com/doselab/>.

EQA 2.1 software. Datasheet [online]. Modus Medical Devices, Inc., 2016 [retrieved on Mar. 28, 2017]. Retrieved from the Internet: <URL: http://modusqa.com/images/resources/MMDI_QUASAR_eQA_PDS.pdf>.

Gao et al., "Evaluation of IsoCal geometric calibration system for Varian linacs equipped with on-board imager and electronic portal imaging device imaging systems," *Journal of Applied Clinical Medical Physics*, 2014, 15(3), Abstract only.

Grzetic et al., "Comparison of seven new TrueBeam linacs with enhanced beam data conformance using a beam comparison software tool," *Med. Phys.*, 2015, Abstract only [online] [retrieved on Mar. 28, 2017]. Retrieved from the Internet <http://scicurve.com/paper/26127873>.

Klein et al., "Task Group 142 report: Quality assurance of medical accelerators," *Med. Phys.*, Sep. 2009, 36(9): pp. 4197-4212.

Kutcher et al., "Comprehensive QA for radiation oncology: Report of AAPM radiation therapy committee task group 40," *Med. Phys.*, Apr. 1994, 21(4): pp. 581-618.

Machine Performance Check software. Product brochure [online]. Varian Medical Systems, Inc., 2016 [retrieved on Mar. 28, 2017]. Retrieved from the Internet: <URL: https://varian.force.com/servlet/servlet.FileDownload?retURL=%2Fapex%2FCpEventPresList%3Fid%3Da0OE000000pZaMdMAK&file=00PE000000VdZFdMAN>.

MyQA™ Machines software. Product brochure [online]. IBA Dosimetry GmbH, 2015 [retrieved on Mar. 28, 2017]. Retrieved from the Internet <URL: http://www.iba-dosimetry.com/sites/default/files/resources/10502-MyQA-Machines_Brochure_215%209x215%209mm_SP.pdf>.

MyQA™ software. Product brochure [online]. IBA Dosimetry GmbH, 2015 [retrieved on Mar. 28, 2017]. Retrieved from the Internet: <URL: http://www.iba-dosimetry.com/sites/default/files/resources/myQA-RT-BR-E-_Rev.1_FINAL.pdf>.

PIPSPRO™ software. Product brochure [online]. Standard Imaging, Inc., 2016 [retrieved on Mar. 28, 2017]. Retrieved from the Internet: <URL: https://www.standardimaging.com/uploads/files/PIPSpro_BR_1251-29.pdf>.

QUALimagiQ software. Product webpage [online]. Qualiformed, [retrieved on Mar. 28, 2017]. Retrieved from the Internet: <URL: http://www.qualiformed.com/qualimagiq>.

Qumulate™ software. About page [online]. Varian Medical Systems, Inc., 2015 [retrieved on Aug. 11, 2016]. Retrieved from the Internet: <URL: https://qumulate.varian.com/about.xhtml>.

RITG142 software. Datasheet [online]. Radiological Imaging Technology, Inc., Nov. 2014 [retrieved on Aug. 11, 2016]. Retrieved from the Internet: <URL: http://www.radimage.com/machine-qa/#TG142>.

Ritter, T., "Tools and techniques for efficiently implementing the recommendations of task group 142," Presentation [online]. University of Michigan, 2015 [retrieved on Mar. 28, 2017]. Retrieved from the Internet: <URL: http://chapter.aapm.org/seaapm/symposia/2015/Ritter.pdf>.

\* cited by examiner

SYSTEMS, METHODS, AND DEVICES FOR COMMISSIONING AND QUALITY ASSURANCE DATA VALIDATION OF RADIATION THERAPY SYSTEMS

FIELD

The present disclosure relates generally to radiation therapy systems, such as a linear accelerator (LINAC) system, and more particularly, to systems, methods, and devices for analysis and validation of data generated during commissioning and quality assurance testing of radiation therapy systems.

BACKGROUND

After installation of a new radiation therapy system, or after major changes thereto, commissioning is performed by an end user (e.g., medical physicist at the radiotherapy site) prior to use of the system for medical treatment. The goal of the commissioning is to provide a treatment planning system (TPS) with beam data of the radiation therapy system, so that a model of the radiation beam can be constructed and used for subsequent dose calculations. Commissioning is the responsibility of the medical physicist and is performed according to national and international standards.

FIG. 2 shows an exemplary process flow for configuration and use of a radiation therapy system, including installation product acceptance 202, commissioning 206, medical treatment 214, and periodic quality assurance 220. After the radiation therapy system is delivered and installed at a new location, it is subject to acceptance testing 204, which is conducted according to a predetermined procedure (e.g., agreed to by the manufacturer and end user) to ensure that the installed system meets the manufacturer's specifications for the system and end-user-specific contract requirements, as well as to ensure the safety of patients and operators during subsequent use of the radiation therapy system.

The data generated by acceptance testing 204 cannot satisfy the requirements of the commissioning process 206 because beam data for commissioning is dependent on the dose calculation algorithms employed by the TPS. Rather, completion of the installation/acceptance testing 202 ensures that the radiation therapy system meets minimal operational criteria. In contrast, commissioning 206 provides for comprehensive measurements of dosimetric parameters and beam data that are used by the TPS in subsequent treatment planning.

After installation product acceptance 202, commissioning 206 involves the acquisition 208 of beam data at different beam energy levels and system configurations (e.g., multi-leaf collimator settings), for example, according to the protocol set forth in the American Association of Physical Medicine (AAPM), Task Group 106 (TG-106), Report entitled "Accelerator Beam Data Commissioning Equipment and Procedures," 2008, which is hereby incorporated by reference herein. The resulting commissioning data is input to a beam configuration module 210 that calculates parameters for one or more dose calculation algorithms to be used by the radiation therapy system. The commissioning data and calculated parameters are uploaded to a dose calculation server (DCS) 212 for subsequent use, for example, a central database for one or more radiation therapy systems at a specific site, such as Varian's distributed dose calculation framework (DDCF).

Radiation therapy planning and delivery to patients can only be performed after commissioning of the system has been completed. To provide radiation treatment 214 to any patient, the data and parameters stored by the DCS 212 can be used by TPS 216 to develop all subsequent instructions (e.g., dosage and device configuration for a desired treatment volume) to treat patients at 218 using the radiation therapy system. Periodically as determined at 230 (e.g., on a daily, weekly, monthly, quarterly, and/or an annual basis), the radiation therapy system is subject to quality assurance (QA) 220, for example, in accordance with AAPM, Task Group 142 (TG-142), Report entitled "Quality Assurance of Medical Accelerators," 2009, which is hereby incorporated by reference herein. At 222, the original commissioning data can be stored as a baseline for later comparison 226 with data 224 reacquired at the time of QA, for example, according to the TG-142 protocol or any other medical physics protocol. The results of the comparison can be provided in a report 228, for example, for use in auditing of some or all of the treatments systems of a particular site or department.

However, this process is not without the possibility of error. Indeed, errors have been known to occur, and it has been suggested by the World Health Organization that as much as 24% of reported radiotherapy incidents with adverse events were due to errors in commissioning (see World Health Organization, "Radiotherapy Risk Profile—Technical Manual). Since the commissioning data is used in dose calculation and treatment planning, an undetected error can affect all of those patients treated before the error is discovered and corrected. Yet the underlying causes of these errors are often not readily determinable during commissioning 206 or later QA 220. For example, systematic errors during the baseline measurements 208 can be repeated during the periodic reacquisition 224, since the same personnel are likely performing both measurements. Thus, even though the original commissioning data 222 is consistent with the reacquired data 224, both sets of data would be erroneous. For example, such a systematic error may be the use of a sensor inappropriate for the radiation field size, which could lead to patients treated with fields of that size receiving higher or lower than desired radiation doses during treatment.

In commissioning 206, users can attempt to identify errors by following system warnings in configuring the beam. However, such warnings are intentionally made lax by the manufacturer of the software used for planning and commissioning to allow for a wide range of different configurations by the end user. Users may also compare their radiation beam data 208 with published beam data or with manufacturer reference data. But such published/reference data tends to be limited to only a few energies or configurations, and thus would not be likely to identify errors at all energies and configurations.

FIG. 3 shows a process flow for configuration and use of a radiation therapy system that was purchased under a contract providing enhanced conformance with factory data and simplified commissioning. The process of FIG. 3 is similar to FIG. 2, except for certain aspects of the installation product acceptance 302, commissioning 306, and periodic quality assurance 320. Only those differences from FIG. 2 are discussed below. In installation product acceptance 302, the testing performed at 304 (e.g., photo-ionization depth) is performed to a tighter tolerance than would normally be required (e.g., in acceptance testing 204 of FIG. 2). After installation product acceptance 302, commissioning 306 relies on the manufacturer's reference beam data 308 instead of separately acquiring beam data 208. Since the acceptance data is not necessarily complete for commissioning and relies on different protocols, the baseline data 322 for subsequent QA 320 may be obtained separately, e.g., by separate acquisition of beam data (similar to 208 of FIG. 2). Nevertheless, the data stored in DCS 212 for treatment planning is the manufacturer reference data rather than acquired data. This may result in substantial time and cost savings in commissioning the radiation treatment system.

Despite the tighter tolerances associated with acceptance testing, the EBC approach is not without issues. For example, EBC controls for photon-ionization depth only, not for other factors that may be relevant to commissioning. Reference beam data from the manufacturer also may not include MLC parameters (e.g., transmission and dosimetric leaf gap (DLG)) or be available for all desired energy levels or field sizes. The user would thus need to measure such parameters and energy levels/field sizes separately for input to beam configuration module 210. Errors during such measurements would thus not be avoided by the EBC process.

Embodiments of the disclosed subject matter may address one or more of the above-noted problems and disadvantages, among other things.

SUMMARY

Embodiments of the disclosed subject matter enable the validation of beam configuration data obtained during the commissioning and/or quality assurance (QA) testing of a radiation therapy device or system. Commissioning data and parameters of other previously-commissioned radiation therapy devices within the radiotherapy community may be sent to a remote commissioning data module, where it is compiled and analyzed. Likewise, QA data and parameters of radiation therapy device within the radiotherapy community may be sent to a remote QA data module (which may be integrated with or separate from the commissioning data module), where it is compiled and analyzed. Data and parameters obtained from a radiation therapy device undergoing commissioning or QA testing can be compared to the compiled data and/or parameters, to factory data and/or parameters, and/or to predetermined device limits, in order to provide an indication to an end user of potential issues or errors. Warnings, feedback, and/or suggestions can be provided to the end user of the radiation therapy device based on the comparison.

In one or more embodiments, a method includes compiling data from a plurality of installed radiation therapy devices. The data can be obtained during respective commissioning of the installed radiation therapy devices. The method can also include performing an analysis of a data set obtained from a radiation therapy device undergoing a commissioning process with respect to the compiled data.

In one or more embodiments, a system includes a commissioning data module having a processor and a memory. The processor can compile data from a plurality of installed radiation therapy devices in the memory. The data can be obtained during respective commissioning of the installed radiation therapy devices. The processor can perform an analysis of a data set obtained from a radiation therapy device undergoing a commissioning process with respect to the compiled data.

In one or more embodiments, there are provided a non-transitory computer-readable storage medium upon which is embodied a sequence of programmed instructions for commissioning validation of a radiation therapy device, and a computer processing system that executes the sequence of programmed instructions embodied on the computer-readable storage medium. Execution of the sequence of programmed instructions can cause the computer processing system to compile data from a plurality of installed radiation therapy devices, and analyze a data set obtained from a radiation therapy device undergoing a commissioning process with respect to the compiled data. The compiled data can be obtained during respective commissioning of the installed radiation therapy devices.

In one or more embodiments, a method includes compiling QA data from a plurality of radiation therapy devices. The QA data can be obtained during respective QA testing of the installed radiation therapy devices. The method can also include performing an analysis of a QA data set obtained from a first one of the installed radiation therapy devices with respect to the compiled QA data.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

In various embodiments, beam data and parameters of previously-commissioned radiation therapy systems within the radiotherapy community may be compiled by a commissioning data module. During commissioning of a new radiation therapy system, the resulting data and parameters can be analyzed by the commissioning data module with respect to the compiled data and parameters, as well as with respect to other information such as, but not limited to, factory data and/or parameters, or predetermined device limits. The commissioning data module can then provide an indication (audio and/or visual) to the end user of the radiation therapy system undergoing commissioning when the data or parameters deviates from the compiled data or parameters, or violates predetermined limits, in order to identify any potential errors before the radiation therapy system is used to treat a patient.

In some embodiments, the commissioning data module can also help the end user troubleshoot the cause of the error, for example, by providing suggestions or a questionnaire to the end user. In some embodiments, the commissioning data module can also serve as a historical repository for changes in device parameters, for example, to help troubleshoot errors during commissioning and/or to provide a restore point to roll back changes that resulted in an error.

Alternatively or additionally, quality assurance (QA) beam data and parameters of radiation therapy systems within the radiotherapy community may be compiled by a QA data module. During periodic (e.g., daily, weekly, monthly, quarterly, or annually) QA testing of a radiation therapy system, the resulting data and parameters can be analyzed by the QA data module with respect to the compiled data and parameters, as well as with respect to other information such as, but not limited to, factory data and/or parameters, or predetermined device limits. The QA data module can then provide an indication (audio and/or visual) to the end user of the radiation therapy system undergoing QA testing when the data or parameters deviates from the compiled data or parameters, or violates predetermined limits, in order to identify any potential errors before the radiation therapy system is next used to treat a patient.

Figure 1:
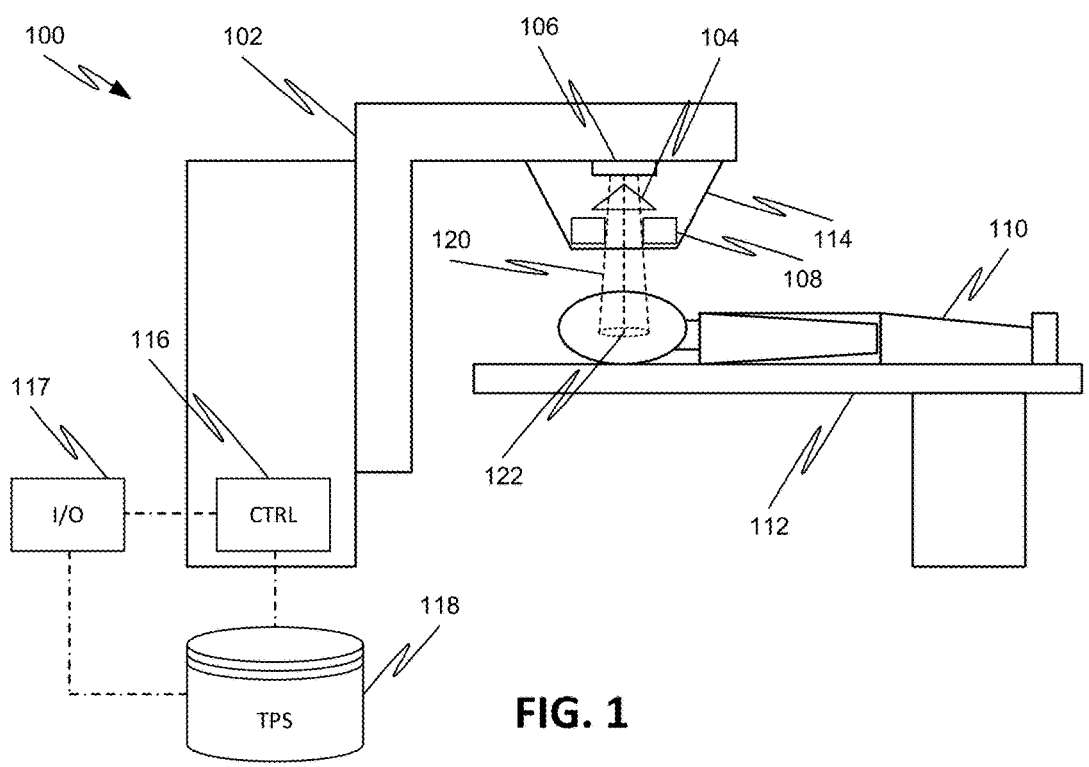
FIG. 1 is a simplified schematic diagram of a radiation therapy system, according to various embodiments of the disclosed subject matter.
Figure 2:
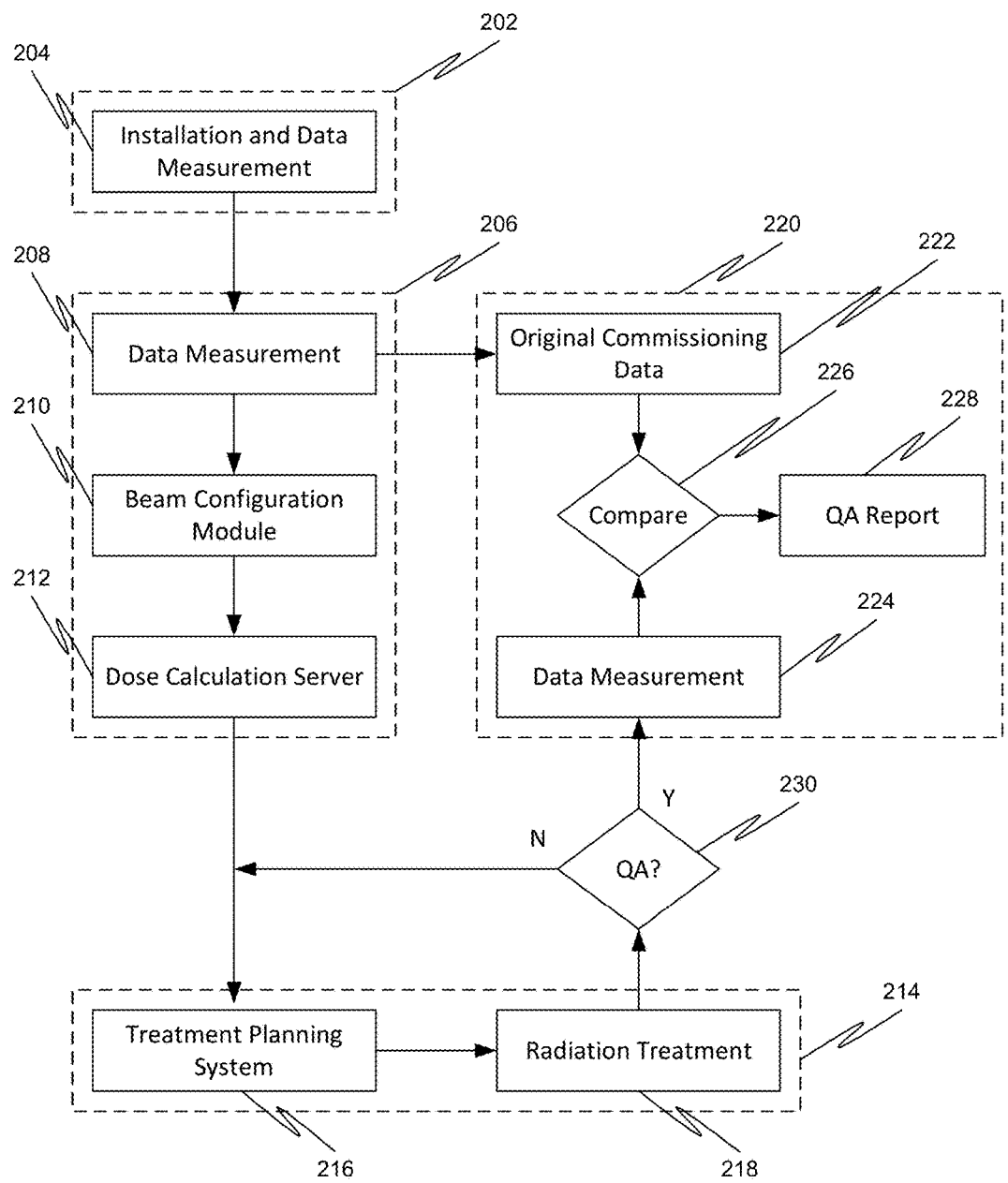
FIG. 2 is a process flow diagram for installation, commissioning, usage, and periodic quality assurance of a radiation therapy system, according to a conventional process.
Figure 3:
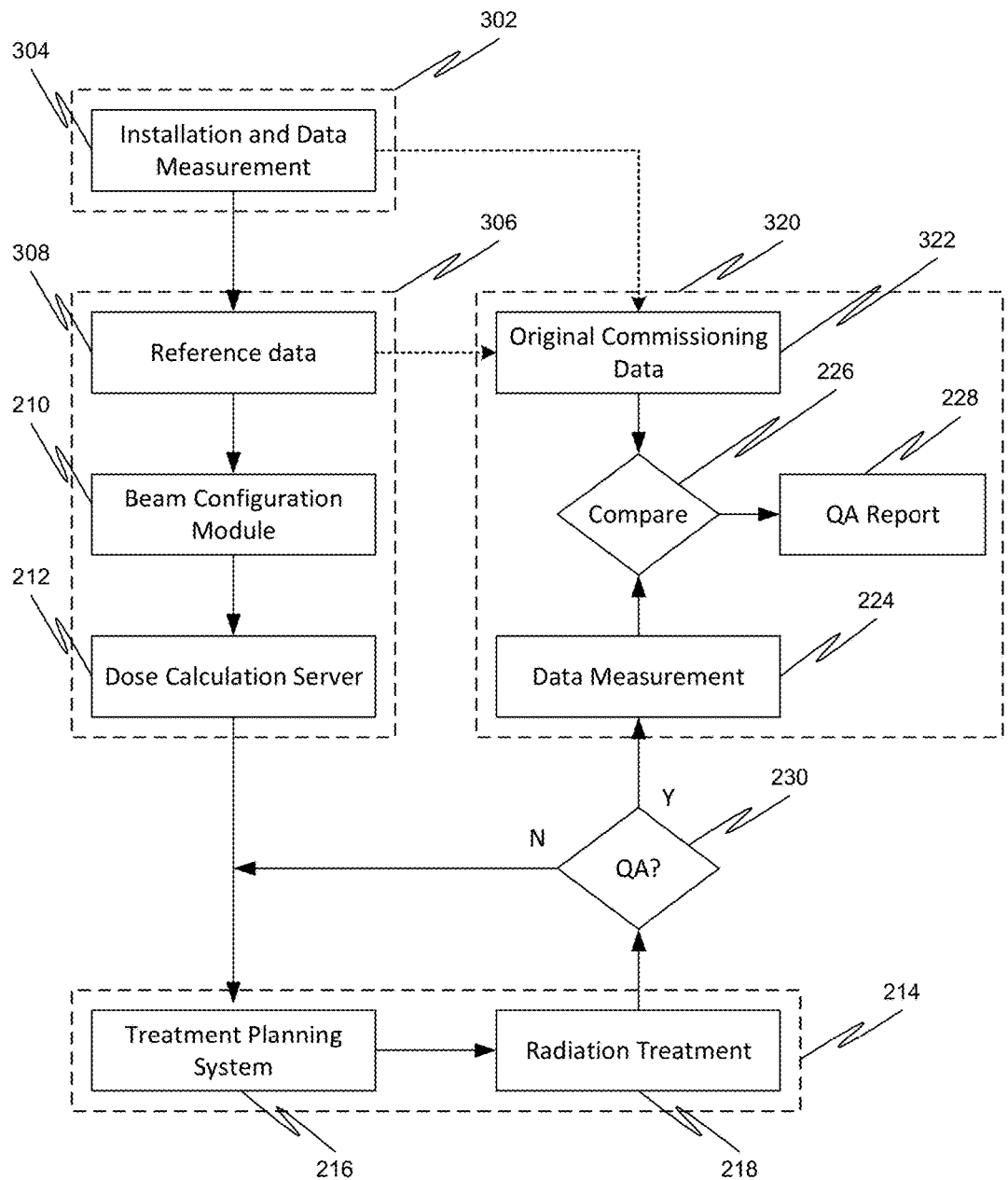
FIG. 3 is a process flow diagram for installation, commissioning, usage, and periodic quality assurance of a radiation therapy system, according to an enhanced conformance and simplified commissioning process.

Referring to FIG. 1, an exemplary radiation therapy system 100 is shown. The therapy system 100 can provide radiation to a patient 110 positioned on a treatment couch 112 and can allow for the implementation of various radiation dose verification protocols. The radiation therapy can include photon-based radiation therapy, particle therapy, electron beam therapy, or any other type of treatment therapy.

In an embodiment, the radiation therapy system 100 can be a radiation treatment device such as, but not limited to, a LINAC operable to generate one or more beams of megavolt (MV) X-ray radiation for treatment. The LINAC may also be operable to generate one or more beams of kilovolt (kV) X-ray radiation, for example, for patient imaging. The system 100 has a gantry 102 supporting a radiation treatment head 114 with one or more radiation sources 106 (e.g., target) and various beam modulation elements, such as, but not limited to, flattening filter 104 and collimating components 108. The collimating components 108 can include, for example, a multi-leaf collimator (MLC), upper and lower jaws, and/or other collimating elements. The collimating components 108 and/or the flattening filter 104 can be positioned within the radiation beam path by respective actuators (not shown), which can be controlled by controller 116.

The gantry 102 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 114 at various rotational and/or axial positions relative to the patient 110 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 108, which can be a computer-controlled mechanical beam shaping device attached to the head 114 and includes an assembly of metal fingers or leaves. For example, the MLC can be made of 120 movable leaves with 0.5 cm and/or 1.0 cm leaf width. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)).

Alternatively or additionally, the radiation therapy device can be a tomotherapy device where intensity modulation is achieved with a binary collimator (not shown) which opens and closes under computer control (e.g., control 116). As the gantry 102 continuously rotates around the patient 110, the exposure time of a small width of the beam can be adjusted with opening and closing of the binary collimator, allowing radiation to be delivered to the treatment volume 122 through the most desirable directions and locations of the patient 110.

Alternatively or additionally, the radiation therapy device can be a helical tomotherapy device, which includes a slip-ring rotating gantry or an intensity modulated arc therapy device (IMAT), which uses rotational cone beams of varying shapes to achieve intensity modulation instead of rotating fan beams. In still another alternative, the radiation therapy device can be a simplified intensity modulated arc therapy (SIMAT) device which uses multiple arcs, or a sweeping window arc therapy device (SWAT), which sweeps the MLC leaf positions across the target planning volume (TPV) with rotation. In yet another alternative, the radiation therapy device can be a volumetric modulated arc therapy (VMAT) device where dose rate, beam aperture shape, and the speed of rotation can be continuously varied to deliver the prescribed dose to the TPV. In yet another alternative, the radiation therapy device can be a volumetric high-definition (or hyperarc) therapy (HDRT) device where does rate, beam aperture shape, speed of rotation and orientation of the patient support can be continuously varied to deliver the prescribed does to the TPV. Indeed, any type of IMRT device can be employed as the radiation therapy device of system 100. For example, embodiments of the disclosed subject matter can be applied to image-guided radiation therapy (IGRT) devices. Each type of radiation therapy device can be accompanied by a corresponding radiation plan and radiation delivery procedure.

The controller 116 can include a computer with appropriate hardware such as a processor, and an operating system for running various software programs and/or communication applications. The controller 116 can include software programs that operate to communicate with the radiation therapy device, which software programs are operable to receive data from external software programs and hardware. The computer can also include any suitable input/output (I/O) devices 117, which can be adapted to allow communication between controller 116 and a user of the radiation therapy system 100, e.g., medical personnel. For example, the controller can be provided with I/O interfaces, storage devices, memory, keyboard, mouse, monitor, printers, scanner, etc.

Alternatively or additionally, the I/O devices 117 can provide access to a network (not shown) for transmitting data between controller 116 and remote systems. For example, the controller 116 can be networked via I/O 117 with other computers and radiation therapy systems. Both the radiation therapy device 100 and the controller 116 can communicate with a network as well as databases and servers, for example, a dose calculation server (e.g., distributed dose calculation framework) and/or a treatment planning system 118 and/or a radiation therapy management system. The controller 116 may also be configured to transfer medical image related data between different pieces of medical equipment.

The system 100 can also include a plurality of modules containing programmed instructions (e.g., as part of controller 116, or as separate modules within system 100, or integrated into other components of system 100), which instructions cause system 100 to perform different functions related to radiation therapy/surgery, as discussed herein, when executed. Computer program code for carrying out operations as described herein may be written in any programming language, for example, C or C++ programming language.

Figure 4A:
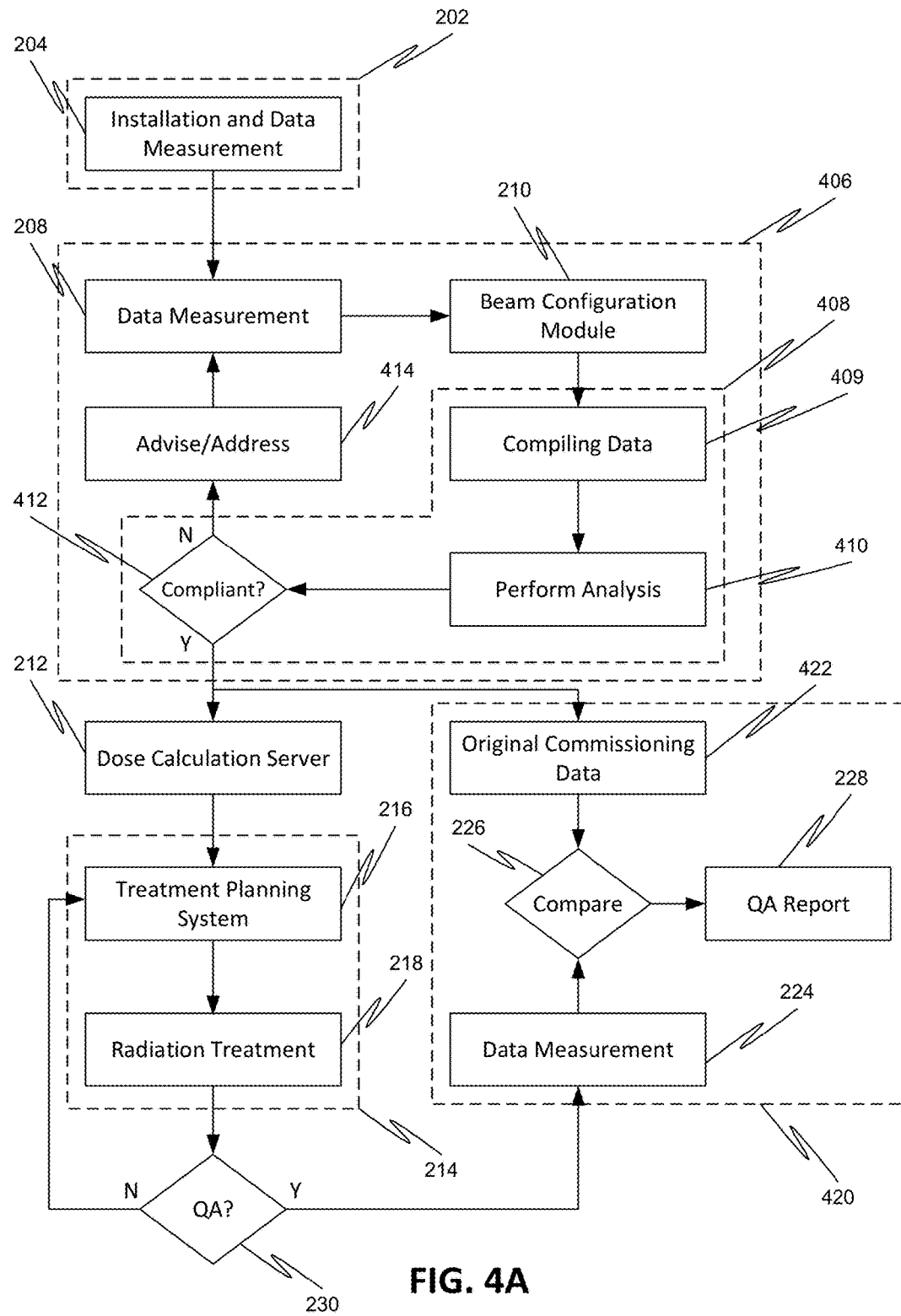
FIG. 4A is a process flow diagram for installation, commissioning, usage, and periodic quality assurance of a radiation therapy system, according to various embodiments of the disclosed subject matter.

FIG. 4A shows an exemplary process flow for configuration and use of a radiation therapy system, including installation product acceptance 202, commissioning 406, medical treatment 214, and periodic quality assurance 420, according to various embodiments of the disclosed subject matter. After the radiation therapy system is delivered and installed at a new location, it is subject to acceptance testing 204, which is conducted according to a predetermined procedure (e.g., agreed to by the manufacturer and end user) to ensure that the installed system meets the manufacturer's specifications for the system and end-user-specific requirements, as well as to ensure the safety of patients and operators during subsequent use of the radiation therapy system.

After installation product acceptance 202, commissioning 406 involves the acquisition 208 of beam data at different beam energy levels and system configurations (e.g., MLC settings), for example, according to the protocol set forth in the AAPM TG-106 Report incorporated by reference above. The resulting commissioning data can be input to a beam configuration module 210, which can automatically extract from the beam data any parameters necessary for one or more dose calculation algorithms to be used by the radiation therapy system. The data and parameters from beam configuration module 210 are provided to commissioning data module 408, which may already have compiled data and parameters 409 from other installed radiation therapy systems.

In various embodiments, the radiation therapy system employs an AAA or AcurosXB dose calculation algorithm. When such algorithms are employed, the commissioning data can include, but is not limited to:
  depth dose curves for a series of radiation field sizes;
  dose profiles for a series of radiation field sizes at a series of depths;
  diagonal dose profiles for the largest radiation field size at a series of depths;
  output factors (i.e., ratio of dose rate at instant field size to dose rate at reference field size) for a series of field sizes at a particular depth;
  measured absolute point dose for a given output, field size, and depth;
  MLC transmission factor; and
  MLC dosimetric leaf gap (DLG).

Radiation therapy systems employing other dose calculation algorithms may include other data or parameters beyond those described above. Accordingly, embodiments of the disclosed subject matter are not limited to the above noted data, parameters, and/or dose calculation algorithms.

In various embodiments, the commissioning data module 408 is provided at a remote site from the radiation therapy system, for example, installed on a network server (e.g., cloud-based module), and communicates with the controller of the radiation therapy system via a wired or wireless network. The provision of data/parameters from the beam configuration module 210 may occur automatically (i.e., without any indication or input from the user) or be initiated by the end user (e.g., by causing the system to upload data over the network, for example, via a computer command or button). Additional information may be communicated with the data/parameters, such as, but not limited to, the name of the end user, the time of the data acquisition or upload, and/or an identification number associated with the radiation therapy system.

The data and parameters from beam configuration module 210 can be analyzed at 410 to determine their compliance, for example, by evaluating with respect to the compiled data and/or with respect to other rules (e.g., hard limits or allowed ranges). If the data and parameters are found to be compliant at 412, the data and parameters are stored in DCS 212 for subsequent use in treatment 214 and in a database 422 (which may be separate from DCS 212) as a baseline for later comparison 226 with data 224 reacquired at the time of QA.

Figure 8:
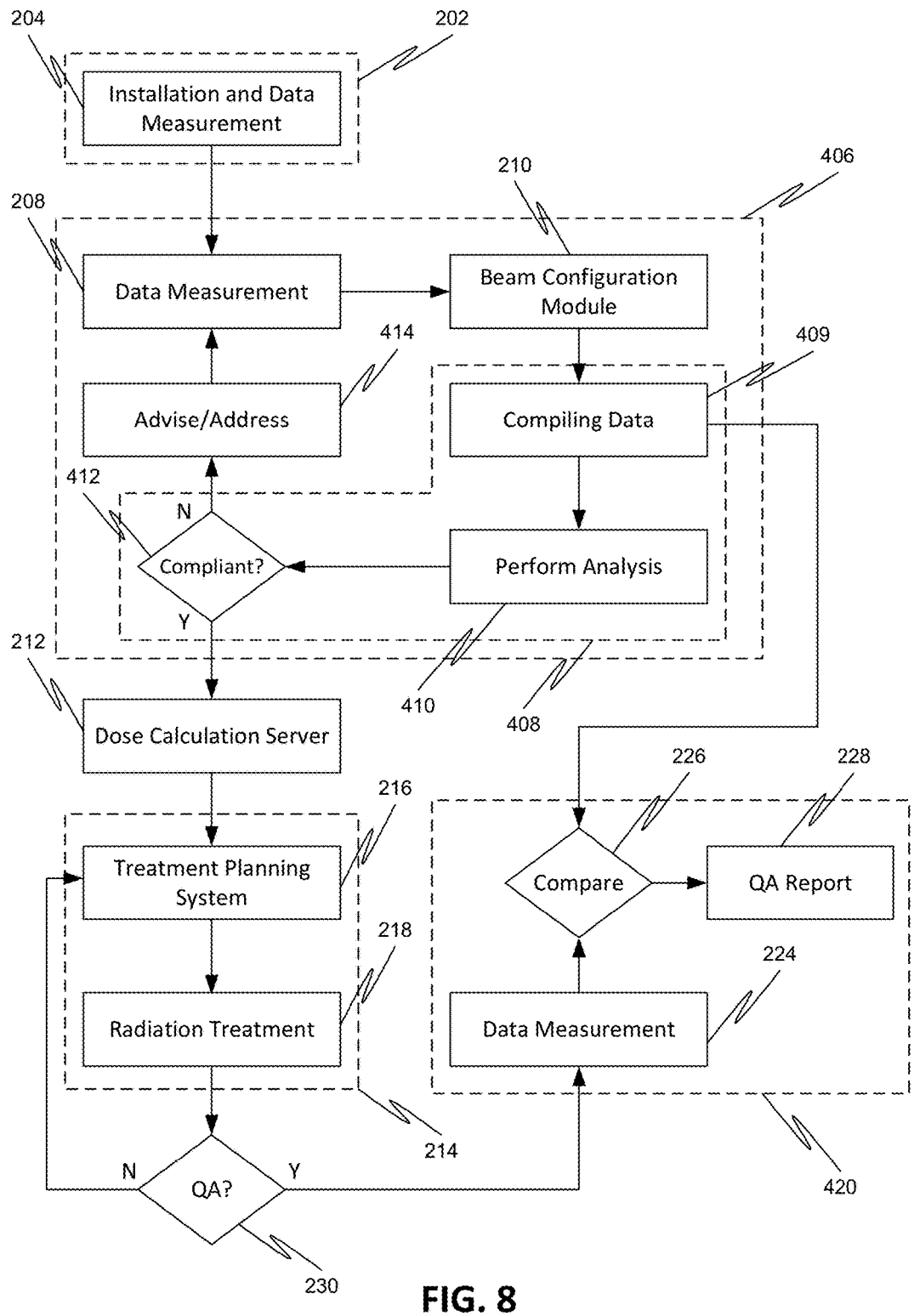
FIG. 8 is a process flow diagram for installation, commissioning, usage, and periodic quality assurance of a radiation therapy system, according to various embodiments of the disclosed subject matter.

The database 422 may obtain the data and parameters from DCS 212 or from the commissioning data module 408. In an alternative configuration illustrated in FIG. 8, the database 422 can be omitted in favor of maintaining the compliant data and parameters with the compiled data (or separate from the compiled data) by the commissioning data module 408 for later download on demand for use in QA 420. In such configurations, the reacquired data at 224 may be processed by beam configuration module 210 for direct comparison of data and parameters with those from the commissioning data module 408.

Returning to FIG. 4A, if the data and parameters are found to be non-compliant at 412, the end user may be advised of the issues (e.g., via audio or visual indicators, such as an audible alarm or on-screen warning) and allowed to address the issues (e.g., by changing configurations or modifying data) at 414. The data may be reacquired at 208 and the process repeated until the data and parameters are found to be compliant at 412, or the end user overrides any determination of non-compliance (as described further below).

Figure 4B:
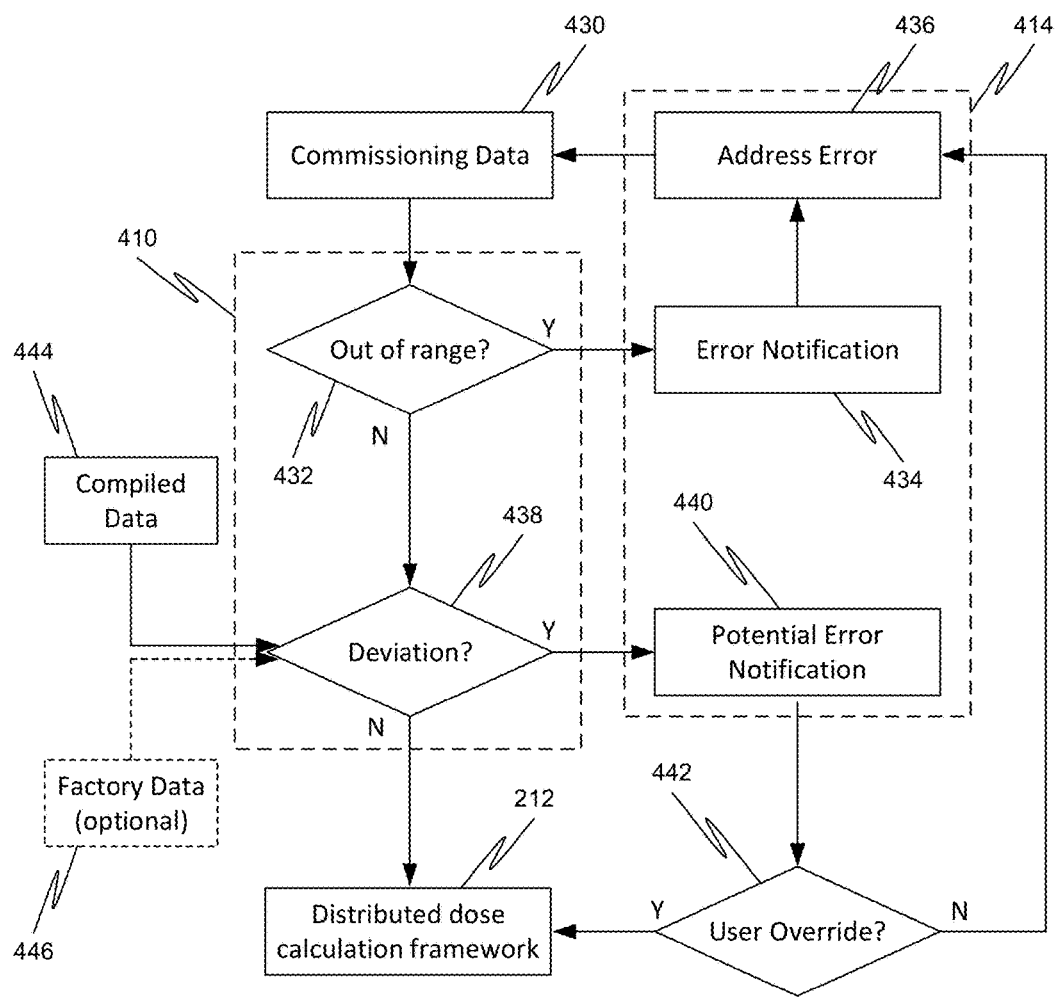
FIG. 4B is a process flow diagram of exemplary analytical and notification aspects of commissioning validation, according to various embodiments of the disclosed subject matter.

FIG. 4B shows exemplary aspects of the analysis 410 and notification 414 functions of the process of FIG. 4A. At 430, the commissioning data from the radiation therapy system can be imported to the commissioning data module, for example, via a network. The commissioning data module can then analyze the data at 432 to determine compliance with predetermined allowable ranges or hard limits associated with the particular type of radiation therapy system. For example, if the uploaded data has a value for MLC transmission factor that is greater than 5%, the MLC transmission factor may be flagged as noncompliant. In another example, the hard limits may be related to measurement values that arise from common errors, for example, where an incorrect sensor has been used for a particular energy setting.

If at 432 the data is determined to be noncompliant, an error notification 434 may be communicated to the end user of the radiation therapy system, for example, by providing an audio or visual indicator. For example, an alarm may sound and/or a display indicate the particular portion of the data that is noncompliant. The error notification 434 can also provide suggestions for possible causes of or resolutions for the error. Based on the error notification 434, the user can address the error at 436 and reacquire the commissioning data at 430, as needed.

If at 432 the data is determined to be compliant with the allowable ranges or hard limits, the commissioning data module can then analyze the data at 438 with respect to compiled data 444. The compiled data 444 can be data and/or parameters obtained during successful commissioning of installed radiation therapy systems, which may be at different sites or departments in the national or global radiotherapy community. Optionally, factory data (e.g., data on the actual radiation therapy system from the manufacturer thereof) or parameters related to factory settings can be provided at 446 for the analysis at 438.

If at 438 the data is determined to comply with the compiled data 444 and/or factory data 446, the commissioning data 430 can be stored in the DCS 212 for subsequent use in treatment planning. The determination of compliance may be based on a statistical analysis of the compiled data, for example. However, if at 438 the data is determined to deviate from the compiled data 444 and/or factory data 446, a potential error notification 440 may be communicated to the user of the radiation therapy system, for example, by providing an audio or visual indicator. For example, an alarm may sound and/or a display indicate the particular portion of the data that deviates from the compiled data. The potential error notification 440 can also provide suggestions for possible causes of or resolutions for the potential error.

Based on the potential error notification 440, the end user can choose to use the uploaded data despite the potential error by overriding at 442. The commissioning data 430 can thus be stored in DCS 212 for subsequent use in treatment planning. If the end user does not override at 442, the user can address the error at 436 and reacquire the commissioning data at 430, as needed.

For example, error notification 434 or potential error notification 440 can include various troubleshooting questions or tips to help the user identify and address the error at 436. For example, the user may be asked if the transmission factor has been measured at 5 cm, since the transmission factor should be measured at 5 cm for energies less than 10 MV but 10 cm for energies greater than or equal to 10 MV. In another example, the user may be asked if a monitor unit setting that is at least 600 monitor units (MU) was used. Alternatively or additionally, the commissioning data module may suggest a protocol to identify the measurement error. In still another example, the user may be asked to confirm that a detector from a list of available detectors was used and/or display a list of allowed detectors. In yet another example, the user may be asked to identify whether a particular measurement refers to central leaves of the MLC or to an average of central and edge leaves.

Figures 6A, 6B:
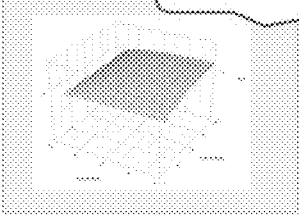
FIGS. 6A-6C illustrate exemplary screen shots displayed to an end user of a radiation therapy system undergoing commissioning, based on analysis of beam data and parameters by the commissioning data module, according to various embodiments of the disclosed subject matter.
Figure 6C:
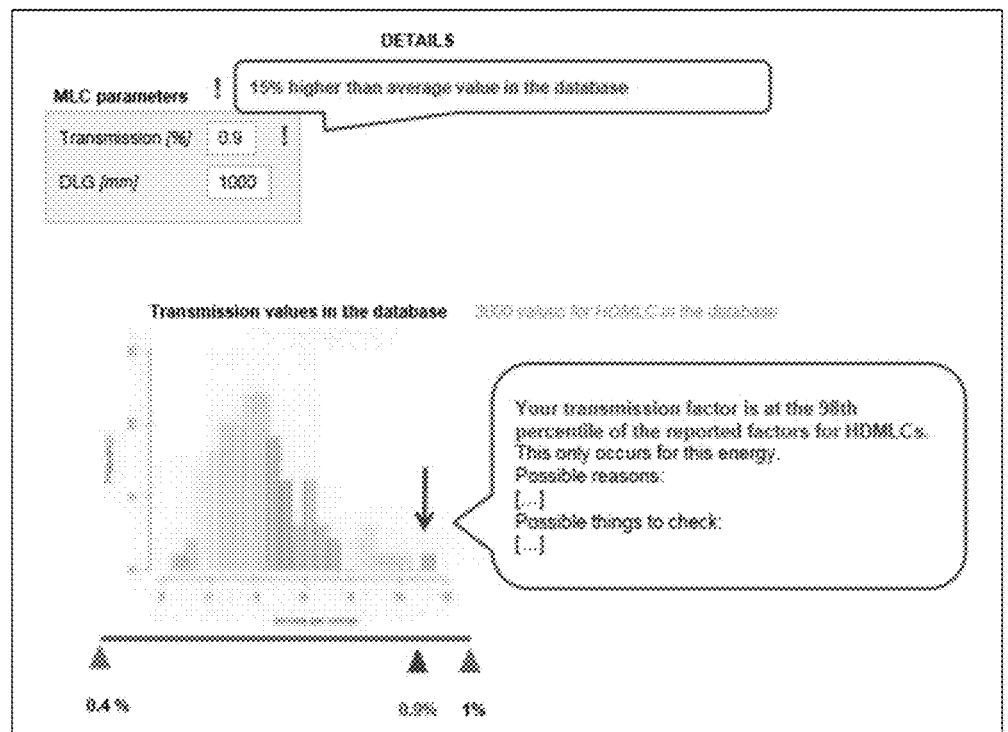

FIGS. 6A-6C are examples of displays generated in response to errors or potential errors with commissioning data. Other troubleshooting and feedback scenarios are also possible according to one or more contemplated embodiments. Accordingly, embodiments of the disclosed subject matter are not limited to the troubleshooting examples explicitly noted above. In various embodiments, the process of FIGS. 4A-4B can automatically detect gross errors that would otherwise have passed through the commissioning process undetected. Such gross errors can include associating a profile with an incorrect energy configuration, e.g., 6×FFF input for 6×. Finer errors can also be detected based on discrepancies from the compiled data.

Figure 7:
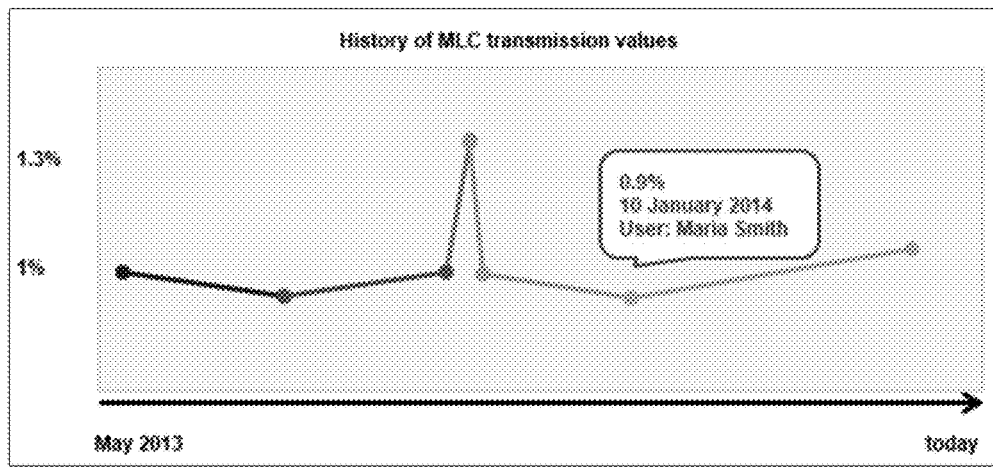
FIG. 7 illustrates an exemplary screen shot of historical changes to a radiation therapy system parameter (e.g., MLC transmission values) during a commissioning process, according to various embodiments of the disclosed subject matter.

In various embodiments, the commissioning data module can provide a history of changes, such as to iteratively updated parameters (e.g., DLG), during the commissioning process. The history can include, for example, timestamp and name of the user initiating the changes, for example, as illustrated in FIG. 7. In the event that an error is revealed in the analysis by the commissioning data module or during subsequent operation of the radiation therapy system, then the history may be used to identify the error. For example, the commissioning data module can provide a trend analysis for various numerical values in the commissioning process, as well as the name of the user who had performed the change. If an error is discovered, the history can be used to identify the user initiating the change, or to revert to a compliant configuration.

Figure 5:
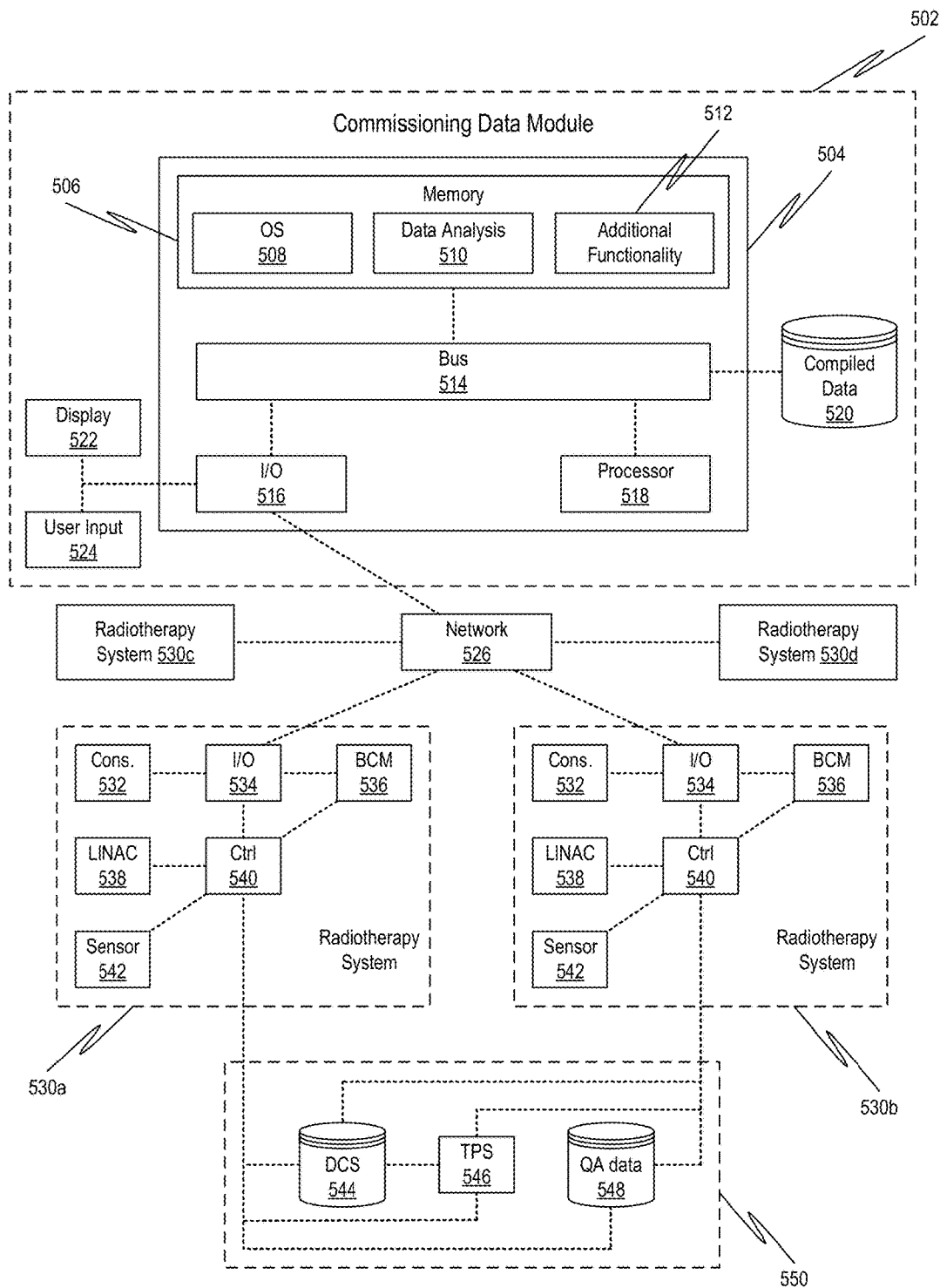
FIG. 5 is a simplified schematic diagram illustrating aspects of a commissioning data module and various radiation therapy systems, according to various embodiments of the disclosed subject matter.

FIG. 5 illustrates aspects of a system employing a commissioning data module 502 according to various embodiments of the disclosed subject matter. Commissioning data module 502 may include, for example, a computer system 504 that can implement one or more aspects of the process of FIGS. 4A-4B and/or FIG. 8. Although shown as a single module 502, the functionality of module 502 can be implemented as a distributed system or otherwise.

For example, the computer system 504 can include a bus 514 or other mechanism for communicating information between components. The computer system 504 can also include a processor 518, for example, a general or specific purpose processor, coupled to bus 514. The computer system 504 can include an input/output module 516, for example, a communication device such as a network interface card that provides access to network 526, and/or input/output ports that allow a user to interact with the computer system 504, for example via user input devices 524 (e.g., mouse, keyboard, etc.) and display 522. A user can thus interact with computer system 504 directly or remotely through network 526 or via any other method.

The computer system 504 can also include a memory 506 that stores information and instructions to be executed by processor 518. The memory 506 can be comprised of any combination of random access memory (RAM), read only memory (ROM), static storage such as a magnetic or optical disk, or any other type of computer readable media. For example, computer readable media may be any available media that can be accessed by processor 518 and can include both volatile and nonvolatile media, removable and non-removable media, and communication media. Communication media may include computer readable instructions, data structures, program modules or other data in a modulated data signal such as a carrier wave or other transport mechanism and includes any information delivery media.

Memory 506 can store software modules that provide functionality when executed by processor 518. The modules can include, for example, an operating system 508, a data analysis module 510, and an additional functionality module 512. The operating system 508 can provide operating system functionality for computer system 504. The data analysis module 510 can receive commissioning data and parameters via I/O 516 and network 526 from one or more radiation therapy systems 530a-530d, and can store the data and parameters in a database 520 for subsequent use or analysis, for example, as described above with respect to FIGS. 4A-4B, 8. Although only four radiation therapy systems are shown in FIG. 5, embodiments of the disclosed subject matter are not limited thereto. Indeed, commercial embodiments of the disclosed subject matter are expected to be connected to and/or incorporate commissioning data from numerous (e.g., tens, hundreds, or even thousands) radiation therapy systems.

For example, commissioning data and parameters from one or more previously installed radiation therapy systems 530c-530d can be communicated to the commissioning data module 502 via network 526 and compiled in database 520 for subsequent use in analyzing commissioning data and parameters for newly installed radiation therapy systems. The one or more radiation therapy systems 530c-530d may be located at separate sites (e.g., hospital or department) from the commissioning data module 502 and/or other radiation therapy systems 530a-530b. In contrast, radiation therapy systems 530a-530b (or other radiation therapy systems not shown) may be installed at a same site and share certain components 550, for example, DCS 544, treatment planning system 546, and/or memory 548 for QA data, which may be connected to each other via an internal network, for example.

For example, each radiation therapy system 530 can include a LINAC 538 operatively coupled to a control module 540 that controls operation thereof. The control module 540 can communicate with network 526 via input/output module 534 to provide data transfer between the control module 540 and the commissioning data module 502, and/or via the shared computer system 550. The input/output module 534 can also communicate with a console 532 that allows an end user to interact with and control operation of the LINAC 538. For example, the console 532 includes one or more audio or visual indicators by which the commissioning data module 502 can provide indication of an error or potential error. For example, the console 532 includes a display and control panel with input devices (e.g., keyboard, mouse, etc.) that allows the user to input commissioning data and to see results of the commissioning data analysis.

One or more sensors 542 (e.g., ion chamber, diodes, or other dosimetric detectors), as well as supporting devices necessary for operation thereof (e.g., electrometers, power supplies, connecting cables, etc.), can be provided as part of each radiation therapy system 530. Alternatively or additionally, sensors 542 can be provided only during commissioning of the radiation therapy system 530 and/or may be moved between systems 530a-530b at the same site as needed. A beam configuration module 536 can receive data generated by sensors 542, for example, as input by the user via console 532 or automatically collected by control module 540. Using the collected beam data, the beam configuration module 536 can generate associated parameters for a selected dose calculation algorithm, which data and parameters may then be communicated to the commissioning data module 502 via input/output module 534.

Although illustrated as separate components, one or more of the components of the radiation therapy system 530 can be combined together or may be part of a single system. For example, the beam configuration module 536 may form part of a computer system that also provides the control module 540. Other configurations are also possible according to one or more contemplated embodiments.

Upon validation of the beam data and parameters by the commissioning data module 502, the beam data and parameters may be transferred to DCS 544, which may be maintained on a computer system or network 550 shared by the various radiation therapy systems installed at a common site or department. The DCS 544 may store the data and parameters for use by TPS 546, which may also be part of a shared computer system or network 550. As noted above, the TPS 546 uses the beam data and parameters to generate a model of the radiation beam for subsequent dose calculations. The commissioning data may also be stored in database 548, which may also be part of a shared computer system or network 550, for periodic quality assurance.

Configurations and components for the commissioning data module, the network, and the radiation therapy systems other than those illustrated in FIG. 5 are also possible according to one or more contemplated embodiments.

In addition to compiling and analyzing commissioning data, embodiments of the disclosed subject matter can also compile and analyze QA data, as described below and with respect to FIGS. 9-10. Periodically (e.g., daily, weekly, monthly, quarterly, annually, or after maintenance service or repairs), QA testing can be performed on the radiation therapy device and the resulting QA data can be compared against baseline values (e.g., data obtained during the commissioning process) to determine whether the radiation therapy device continues to operate within established limits or tolerances. Although the QA data is not used for treatment planning, periodic QA testing ensures that the delivered radiation dose to the patient remains within allowable limits (e.g., that the dose received by the patient is within 5% of the prescribed dose). QA data that violates these established tolerances can be indicative of machine malfunction, mechanical breakdown, physical accidents, component failure or aging (perhaps requiring replacement), operator error, or the like.

The tolerances may be selected based on the type of radiation therapy device (e.g., non-IMRT versus IMRT versus stereotactic radiosurgery (SRS), etc.), with different machine types having different tolerances. For example, under TG-142, the tolerance for coincidence of radiation and machine isocenter is 2 mm for non-IMRT and IMRT machines and 1 mm for SRS machines. The tolerances may also be selected based on the period (e.g., daily, weekly, monthly, quarterly, annually, etc.) of the QA testing. For example, more frequent QA testing protocols (e.g., daily) may employ a less precise measurement methodology than less frequent QA testing protocols (e.g., annual). The selected tolerances may thus take into account the different precision of the underlying QA test. Selection of tolerances may be automatically performed (e.g., by the QA data module). Additionally or alternatively, the tolerances may also be customized by a user or an institution operating the radiation therapy device. In general, such custom tolerances would be stricter than those otherwise required by applicable standards.

In addition to the comparison of QA data with baseline data (e.g., commissioning data), embodiments of the disclosed subject matter may also compare QA data with previous QA data for that particular radiation therapy device and/or compiled QA data for other radiation therapy devices. QA data may be sent from each radiation therapy device to a common QA data module, similar to the commissioning data module, where it is compiled and analyzed. For example, QA data from radiation therapy devices of a particular machine type (e.g., non-IMRT, IMRT, SRS, etc.) can be compiled together by the QA data module. Alternatively or additionally, radiation therapy devices installed at a common site (e.g., department or hospital) or operated by a common institution (e.g., hospital network or connected to a common system) can be grouped together and respective QA data from each group compiled. The compiled data can be analyzed by the QA data module to provide insight into machine operation and can be used as a basis for comparing new QA data from new or existing radiation therapy devices.

For example, a statistical analysis of the compiled data can be performed to determine optimal tolerances for the baseline comparison. When there is little compiled data in the system, the initial tolerances set by the QA data module may be somewhat lax, although still within the limits defined by the industry standards (e.g., TG-142). However, as the number of QA data entries increases, the statistical analysis can indicate which tolerances should be tightened to reflect normal operation. The QA data module may periodically or continuously update the tolerances applied based on this statistical analysis.

The QA data module may also track changes in QA data over time. Such changes can be communicated by the QA data module to the end user of the radiation therapy device, for example, by displaying as a graph to the end user. Thus, the QA data module can provide information regarding drift over time as well as information regarding deviations from baseline. The former is relevant in that it can help detect ongoing processes compromising the treatment quality, even though the system at any given snapshot is well within tolerance. Alternatively or additionally, the QA data module may provide tags of relevant information for each QA data entry or change in QA data (e.g., date, user, component maintenance status).

The QA data module may also track maintenance or service records of the radiation therapy device. For example, information on replacement/service of a component of the radiation therapy device may be stored by the QA data module, and changes in QA data may be correlated to the replacement/service. If replacement/service of a component caused a particular QA variable to change from non-compliant to compliant for a radiation therapy device, the QA data module may suggest such replacement/service when another radiation therapy device is similarly non-compliant.

In some embodiments, a manufacturer of radiation therapy devices (or a maintenance/service provider thereof) may use the QA data module as an investigative and/or communicative platform. For example, information regarding known issues with specific components (e.g., due to aging) can be posted through the QA data module. Such information may be correlated with specific QA data patterns. For example, a particular QA data variable exceeding the established tolerances may indicate excessive wear of a particular component of the radiation therapy device. Alternatively, a QA data variable that trends toward a particular threshold may be indicative of component wear that will eventually require replacement. The QA data module may thus provide a notification to the end user that the component should be replaced, or give a projected lifetime for that component based on the current trend. Other notifications from the manufacturer, such as indications regarding overdue items on standard maintenance schedule, can also be provided by the QA data module, even if such items are not correlated with specific QA data patterns. Moreover, the end user may use the QA data module to communicate information to the manufacturer or maintenance service provider, for example, by requesting service or sending QA data results in anticipation of upcoming service.

Figure 9:
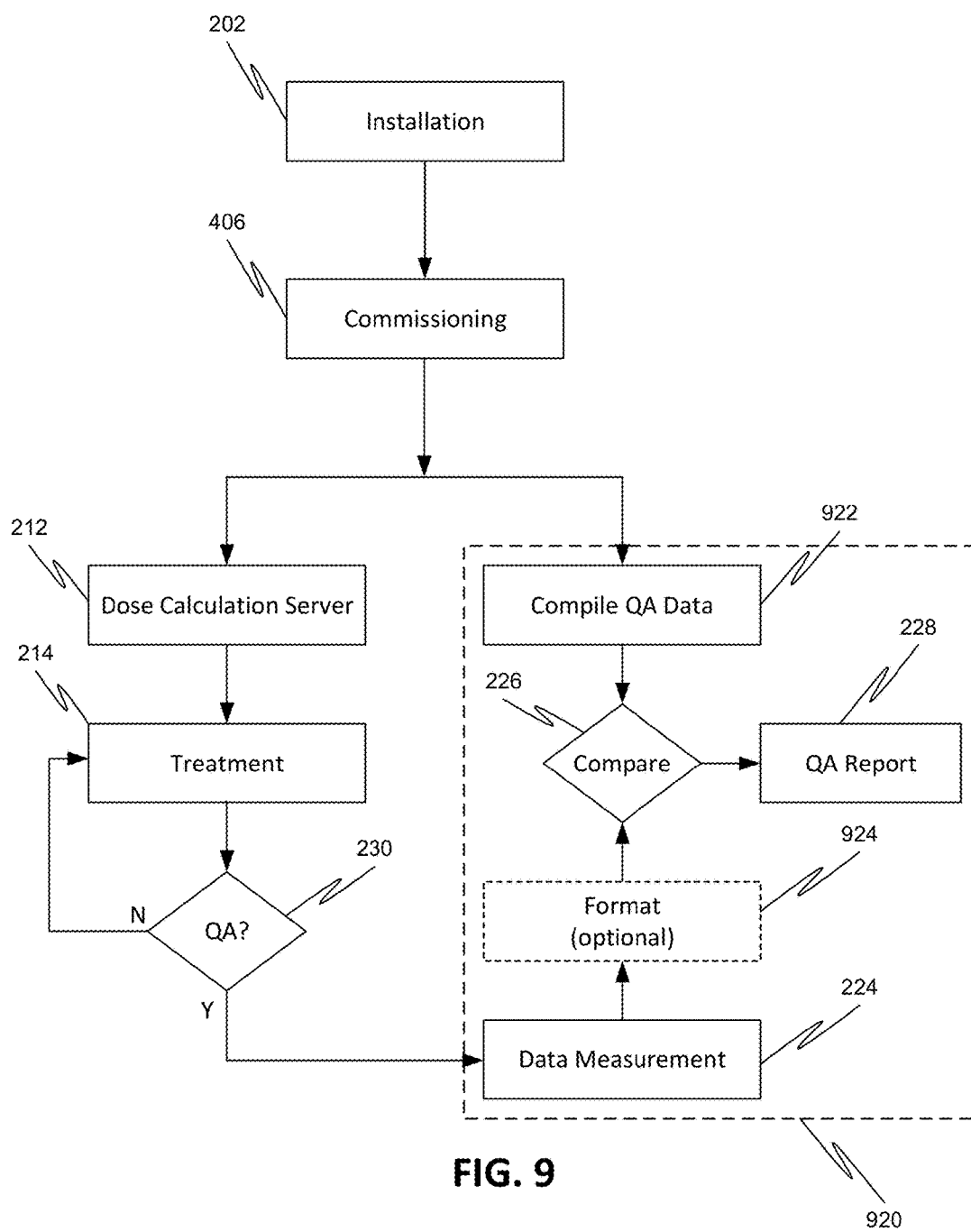
FIG. 9 is a process flow diagram illustrating aspects of quality assurance validation, according to various embodiments of the disclosed subject matter.

Referring to FIG. 9, an exemplary process flow focusing on the QA aspects of operation of a radiation therapy system is shown. Note that the installation 202, commissioning 406 (or 206 or 306), dose calculation 212, and treatment 214 aspects of the process flow of FIG. 9 may be similar to those features of FIGS. 2-4B and/or 8. In other words, the QA aspects of FIG. 9 may be integrated with the process flows of any of FIGS. 2-4B and 8. Alternatively, the QA aspects illustrated in FIG. 9 may exist separately and operate independently of the installation/commissioning/treatment features described with respect to FIGS. 2-4B and 8. The description below thus focuses only on the QA process 920.

At 922, the original commissioning data can be stored as a baseline for later comparison 226 with data 224 reacquired at the time of QA, for example, according to the TG-142 protocol or any other medical physics protocol. However, as noted above, the QA data obtained at 224 is uploaded (either automatically or via initiation by an end user) to a QA data module, which may include a central database connected to the radiation therapy device via a network (see FIG. 10). Optionally, the QA data can be formatted at 924 to allow processing by the QA data module regardless of the underlying manufacturer or operating software of the radiation therapy device. For example, software can be used to convert the QA data to a common format employed by the QA data module for compiling and analysis. The baseline data 922 may also be stored by the QA data module. Thus, the QA data module can perform comparison 226 and generate report 228, as well as provide comparison of QA data to other radiation therapy devices and provide a trend analysis of QA data for the radiation therapy device with respect to time and/or maintenance. FIG. 10 illustrates aspects of a system employing a QA data module 1002 according to various embodiments of the disclosed subject matter. QA data module 1002 may include, for example, a computer system 1004 that can implement one or more aspects of the process of FIG. 9. Although shown as a single module 1002, the functionality of module 1002 can be implemented as a distributed system or otherwise. Moreover, although illustrated separately, the QA data module 1002 and the commissioning data module 502 (FIG. 5) may be integrated together, for example, as a single module with both QA and commissioning data functionality provided by memory 506/1006, as separate parts of a common computer system 504/1004, or as separate parts of a common system (e.g., a central or distributed processing system operating on a remote server).

For example, the computer system 1004 can include a bus 1014 or other mechanism for communicating information between components. The computer system 1004 can also include a processor 1018, for example, a general or specific purpose processor, coupled to bus 1014. The computer system 1004 can include an input/output module 1016, for example, a communication device such as a network interface card that provides access to network 526 (which may be the same network by which the commissioning data module communicates with each radiation therapy system 530), and/or input/output ports that allow a user to interact with the computer system 1004, for example via user input devices 1024 (e.g., mouse, keyboard, etc.) and display 1022. A user can thus interact with computer system 1004 directly or remotely through network 526 or via any other method.

The computer system 1004 can also include a memory 1006 that stores information and instructions to be executed by processor 1018. The memory 1006 can be comprised of any combination of random access memory (RAM), read only memory (ROM), static storage such as a magnetic or optical disk, or any other type of computer readable media. For example, computer readable media may be any available media that can be accessed by processor 1018 and can include both volatile and nonvolatile media, removable and non-removable media, and communication media. Communication media may include computer readable instructions, data structures, program modules or other data in a modulated data signal such as a carrier wave or other transport mechanism and includes any information delivery media.

Memory 1006 can store software modules that provide functionality when executed by processor 1018. The modules can include, for example, an operating system 1008, a data analysis module 1010, and an additional functionality module 1012. The operating system 1008 can provide operating system functionality for computer system 1004. The data analysis module 1010 can receive QA data and parameters via I/O 1016 and network 526 from one or more radiation therapy systems 530a-530d, and can store the QA data and parameters in a database 1020 for subsequent use or analysis, for example, as described above with respect to FIG. 9.

Figure 10:
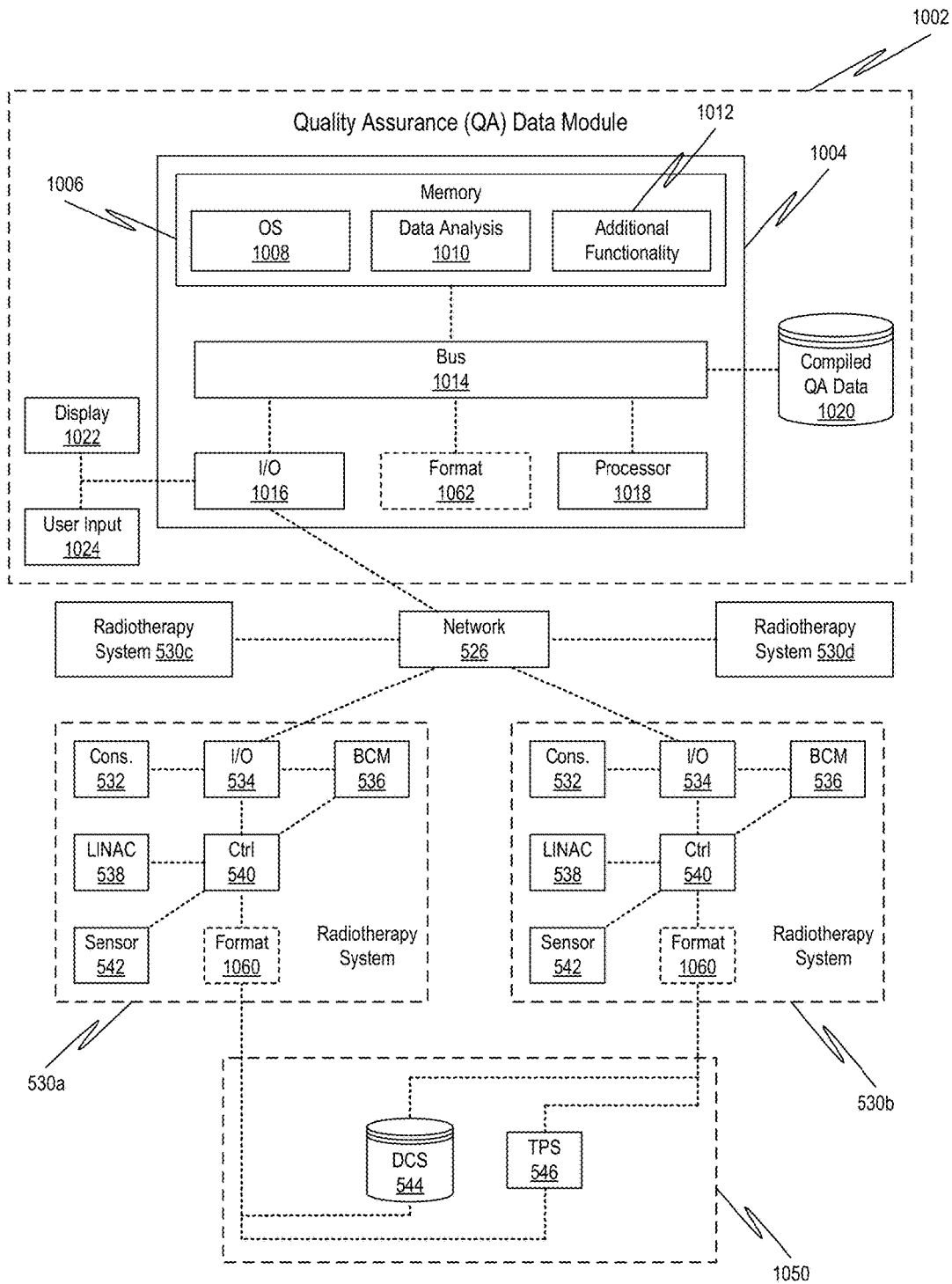
FIG. 10 is a simplified schematic diagram illustrating aspects of a quality assurance data module and various radiation therapy systems, according to various embodiments of the disclosed subject matter.

Although only four radiation therapy systems are shown in FIG. 10, embodiments of the disclosed subject matter are not limited thereto. Indeed, commercial embodiments of the disclosed subject matter are expected to be connected to and/or incorporate QA data from numerous (e.g., tens, hundreds, or even thousands) radiation therapy systems.

For example, QA data and parameters (and, in some embodiments, baseline commissioning data and parameters) from one or more previously installed radiation therapy systems 530c-530d can be communicated to the QA data module 1002 via network 526. The QA data may be formatted by the radiation therapy system 530, for example, by a formatting module 1060 prior to upload via network 526, or by a formatting module 1062 of QA data module 1002 after upload via network 526.

The data analysis module 1010 may process the formatted data to compile it based on machine type, location (e.g., department or hospital), operator system (e.g., hospital network), or any other criteria, and to store the compiled data in database 1020. The data analysis module may be further configured to perform a comparison of the QA data with its corresponding baseline data (e.g., commissioning data) and to compare to established tolerances (which the data analysis module 1010 may vary over time based on a statistical analysis of the compiled data) and to generate a report for use by the end user in auditing of the radiation therapy device. The data analysis module 1010 may also be configured to provide a comparison of QA data to other radiation treatment devices and/or to provide a trend analysis of QA data with respect to time and/or maintenance.

The additional functionality module 1012 may be configured to provide other functions that supplement or are outside the scope of the functions performed by the data analysis module 1010. For example, either the additional functionality module 1012 or the data analysis module 1010 can be configured to provide the investigative/communicative functions noted above.

The one or more radiation therapy systems 530c-530d may be located at separate sites (e.g., hospital or department) from the QA data module 1002 and/or other radiation therapy systems 530a-530b. In contrast, radiation therapy systems 530a-530b (or other radiation therapy systems not shown) may be installed at a same site and share certain components 1050, for example, DCS 544 and treatment planning system 546, which may be connected to each other via an internal network, for example.

Configurations and components for the QA data module, the network, and the radiation therapy systems other than those illustrated in FIG. 10 are also possible according to one or more contemplated embodiments.

Various embodiments of the disclosed subject matter can enable a seamless comparison of beam data and models across the radiotherapy community and can provide one or more of the following functionalities:

automatic upload of beam data and parameters from the beam configuration workspace to a central database (e.g., commissioning data module) for analysis, storage, and/or compilation for use in analyzing other systems' beam data;

end-user initiated upload of beam data and parameters from the beam configuration workspace to a central database (e.g., commissioning data module) for analysis, storage, and/or compilation for use in analyzing other systems' beam data;

allow the end user to view the consistency of their beam data;

allow the end user to view the similarity of their beam data and models with the community and/or reference beam data, using statistical measurements (e.g., percentile, histogram) for different selectors (e.g., region, machine type, MLC type, energy);

provide feedback in the form of warnings and suggestions to the end user;

provide a history of changes and name of the user initiating each change, for example, to assist in root cause analysis in case of detected errors;

compare machine settings to factory data for the machine or to related parameters of the factory settings;

allow third party queries (e.g., from the manufacturer or a maintenance service provider) for accessing end user beam data and parameters, or for analysis and design improvements to design of the radiation therapy system;

upload (either automatic or end user initiated) of additional information not otherwise included with beam data, such as chamber type, whether MLC parameters refer to inner leaves only or an average, or any other relevant information;

download of previously stored data, either stored by user (e.g., used to revert to a previous configuration) or stored by another user of the community;

link to actual customer information or manufacturer documentation in the event of determined discrepancy or error;

allow end users to access data from multiple locations;

provide secure record keeping of data;

with respect to QA aspects, allow monitoring of system drift over time in addition to deviations from baseline;

with respect to QA aspects, allow an end user to define tolerances, for example, a TG-142 protocol or a custom set of tighter tolerances;

with respect to QA aspects, allow evolving tolerances that can tighten over time as more QA data is compiled and analyzed by the system;

with respect to QA aspects, allow tracking of service or maintenance and the associated changes in system performance with respect to QA aspects, allow communication between the manufacturer or regulator and end user regarding known issues with specific components and/or outstanding maintenance/service requirements.

In one or more first embodiments, a method comprises compiling data from a plurality of installed radiation therapy devices. The data can be obtained during respective commissioning of the installed radiation therapy devices. The method can further comprise performing an analysis of a first data set obtained from a first radiation therapy device undergoing a commissioning process with respect to the compiled data.

In the first embodiments, or any other disclosed embodiment, the installed radiation therapy devices and the first radiation therapy device comprise respective linear accelerators.

In the first embodiments, or any other disclosed embodiment, the method further comprises providing auditory and/or visual indications based on said analysis. In the first embodiments, or any other disclosed embodiment, providing an indication of a potential error includes displaying a list of one or more potential causes for the deviation. In the first embodiments, or any other disclosed embodiment, the indication of a potential error comprises an on-screen warning to an operator of the first radiation therapy device performing the commissioning process.

In the first embodiments, or any other disclosed embodiment, when the analysis finds that the first data set violates predetermined limits, an indication of an error is provided. In the first embodiments, or any other disclosed embodiment, when the analysis finds that the first data set deviates from the compiled data by more than a predetermined threshold without violating the predetermined limits, an indication of a potential error is provided. In the first embodiments, or any other disclosed embodiment, when the analysis finds that the first data set does not violate the predetermined limits and has a deviation from the compiled data less than the predetermined threshold, the first data set is saved as commissioning data for the first radiation therapy device and/or sent to a dose calculation server.

In the first embodiments, or any other disclosed embodiment, the data comprises irradiation beam data from the installed radiation therapy devices and corresponding system parameters. In the first embodiments, or any other disclosed embodiment, the irradiation beam data includes at least one of depth dose curves, dose profiles, output factor, and absolute point dose. In the first embodiments, or any other disclosed embodiment, the system parameters include at least one of field size, beam energy, sensor chamber type, source-surface distance (SSD), sensor depth, multi-leaf collimator (MLC) transmission factor, MLC dosimetric leaf gap (DLG), type of MLC, and type of dose calculation algorithm.

In the first embodiments, or any other disclosed embodiment, the first data set is obtained by a beam configuration module that calculates parameters for a selected dose calculation algorithm for the first radiation therapy device. In the first embodiments, or any other disclosed embodiment, the calculated parameters and the first data set are used by a dose calculation server to calculate dose for irradiation of a patient by the first radiation therapy device.

In the first embodiments, or any other disclosed embodiment, the compiling includes storing data in a common storage medium separate from at least one of the installed radiation therapy devices. In the first embodiments, or any other disclosed embodiment, the first data set is automatically transmitted from a first site where the first radiation therapy device is installed to the common storage medium, and the analysis is performed by a processor at a second site separate from the first site.

In the first embodiments, or any other disclosed embodiment, the method further comprises communicating results of said analysis to an operator of the first radiation therapy device.

In the first embodiments, or any other disclosed embodiment, the first data set includes a name or ID of an operator of the first radiation therapy device and a time stamp associated therewith.

In the first embodiments, or any other disclosed embodiment, the compiled data includes a history of changes to the installed and/or first radiation therapy devices and a name or ID of operators initiating the changes.

In the first embodiments, or any other disclosed embodiment, the method further comprises analyzing the first data set with respect to factory data of the first radiation therapy device and/or with related parameters of factory settings.

In the first embodiments, or any other disclosed embodiment, the method further comprises measuring the first data set during the commissioning process of the first radiation therapy device. In the first embodiments, or any other disclosed embodiment, the method further comprises, when the analysis finds that the first data set violates predetermined limits, requiring measurement of a second data set for the first radiation therapy device and repeating the analysis on the second data set. In the first embodiments, or any other disclosed embodiment, the method further comprises, when the analysis finds that the first data set deviates from the compiled data by more than a predetermined threshold without violating predetermined limits, obtaining operator authorization to send the first data set to a dose calculation server for subsequent use in calculating dose for irradiation of a patient, or requiring measurement of a second data set for the first radiation therapy device and repeating the analysis on the second data set.

In the first embodiments, or any other disclosed embodiment, when the analysis finds that the first data set does not violate predetermined limits and has a deviation from the compiled data less than a predetermined threshold, the first data set is saved in the common storage medium for periodic quality assurance and/or in a dose calculation server for irradiation dose calculation.

In one or more second embodiments, a non-transitory computer-readable storage medium and a computer processing system are provided. The computer readable storage medium has embodied thereon a sequence of programmed instructions for commissioning validation of a radiation therapy device. The computer processing system executes the sequence of programmed instructions embodied on the computer readable storage medium to cause the computer processing system to perform the method (or parts thereof) of one or more of the first embodiments.

In one or more third embodiments, a system comprises a commissioning data module, which comprises a processor and a first memory. The processor is configured to compile data from a plurality of installed radiation therapy devices in the first memory, said data being obtained during respective commissioning of the installed radiation therapy devices. The processor is further configured to perform an analysis of a first data set obtained from a first radiation therapy device undergoing a commissioning process with respect to the compiled data.

In the third embodiments, or any other disclosed embodiment, the system further comprises the first radiation therapy device, wherein the first radiation therapy device is a linear accelerator having a multi-leaf collimator (MLC).

In the third embodiments, or any other disclosed embodiment, the system further comprises a beam configuration module configured to calculate parameters for a selected dose calculation algorithm for the first radiation therapy device and to generate the first data set. In the third embodiments, or any other disclosed embodiment, the system further comprises a dose calculation server with a second memory configured to store data and/or parameters from the beam configuration module.

In the third embodiments, or any other disclosed embodiment, the system further comprises a second memory for use by the first radiation therapy device and separate from the first memory. The processor is configured to send the first data set to the second memory for storage therein when the analysis indicates that the first data set is compliant or is otherwise approved by a user of the first radiation therapy device.

In the third embodiments, or any other disclosed embodiment, the system further comprises a network operatively connected to the commissioning data module, the first radiation therapy device, and/or at least one of the installed radiation therapy devices. The network is configured to transmit data to/from connected devices and/or module.

In the third embodiments, or any other disclosed embodiment, the system further comprises a controller of the first radiation therapy device. The controller is configured to automatically transmit the first data set to the commissioning data module.

In the third embodiments, or any other disclosed embodiment, the system further comprises a control panel configured such that an operator controls operation of the first radiation therapy device during the commissioning process.

In the third embodiments, or any other disclosed embodiment, the system further comprises one or more sensors disposed so as to detect irradiation beam data for the first data set during the commissioning process.

In the third embodiments, or any other disclosed embodiment, the system further comprises audio and/or visual indicators for communicating results of said analysis to an operator of the first radiation therapy device. In the third embodiments, or any other disclosed embodiment, the visual indicator comprises a display screen.

In the third embodiments, or any other disclosed embodiment, the processor is configured to, when the analysis finds that the first data set violates predetermined limits, provide an indication of an error. In the third embodiments, or any other disclosed embodiment, the processor is configured to, when the analysis finds that the first data set deviates from the compiled data by more than a predetermined threshold without violating the predetermined limits, provide an indication of a potential error. In the third embodiments, or any other disclosed embodiment, the processor is configured to, when the analysis finds that the first data set does not violate the predetermined limits and has a deviation from the compiled data less than the predetermined threshold, save the first data set as commissioning data for the first radiation therapy device and/or send to a dose calculation server.

In the third embodiments, or any other disclosed embodiment, the indication of a potential error includes displaying a list of one or more potential causes for the deviation.

In the third embodiments, or any other disclosed embodiment, the processor is configured to analyze the first data set with respect to factory data of the first radiation therapy device and/or with related parameters of factory settings.

In one or more fourth embodiments, a method comprises compiling quality assurance (QA) data from a plurality of radiation therapy devices. The QA data is obtained during respective QA testing of the radiation therapy devices. The method further comprises performing an analysis of a first QA data set obtained from a first one of the radiation therapy devices with respect to the compiled QA data.

In the fourth embodiments, or any other disclosed embodiment, the method further comprises compiling commissioning data from the plurality of radiation therapy devices. The commissioning data is obtained during respective commissioning of the plurality of the radiation therapy devices. The method further comprises performing an analysis of a first data set obtained from the first one of the radiation therapy device during commissioning thereof with respect to the compiled commissioning data.

In the fourth embodiments, or any other disclosed embodiment, the radiation therapy devices comprise respective linear accelerators.

In the fourth embodiments, or any other disclosed embodiment, when the analysis finds that the first QA data set violates predetermined limits, an indication of an error is provided. In the fourth embodiments, or any other disclosed embodiment, the predetermined limits can be set by a user of the first one of the plurality of the radiation therapy devices, and/or are selected based on a machine type of the first one of the plurality of the radiation therapy devices.

In the fourth embodiments, or any other disclosed embodiment, in the compiling, QA data from radiation therapy devices installed in a same department or location are grouped together, and/or QA data from radiation therapy devices connected to a common dose calculation server or treatment planning system are grouped together.

In the fourth embodiments, or any other disclosed embodiment, the compiled QA data includes service or maintenance records for the radiation therapy devices.

In the fourth embodiments, or any other disclosed embodiment, the performing the analysis includes providing a visual depiction of changes in the QA data for the first one of the radiation therapy devices over time. In the fourth embodiments, or any other disclosed embodiment, the changes are tagged with a corresponding date and username of the first one of the radiation therapy devices.

In the fourth embodiments, or any other disclosed embodiment, the data comprises irradiation beam data from the installed radiation therapy devices and corresponding system parameters.

In the fourth embodiments, or any other disclosed embodiment, the compiling includes storing data in a common storage medium separate from the first one of the radiation therapy devices. In the fourth embodiments, or any other disclosed embodiment, the first QA data set is automatically transmitted from a first site where the first one of the radiation therapy devices is installed to the common storage medium, and the analysis is performed by a processor at a second site separate from the first site.

In the fourth embodiments, or any other disclosed embodiment, the method further comprises generating a QA report based on the analysis of the first QA data set.

In one or more fifth embodiments, a non-transitory computer-readable storage medium and a computer processing system are provided. The computer readable storage medium has embodied thereon a sequence of programmed instructions for QA data validation of a radiation therapy device. The computer processing system executes the sequence of programmed instructions embodied on the computer readable storage medium to cause the computer processing system to perform the method (or parts thereof) of one or more of the fourth embodiments.

In one or more sixth embodiments, a system comprises a QA data module, which comprises a processor and a memory. The processor is configured to compile QA data from a plurality of radiation therapy devices in the memory. The QA data can be obtained during respective QA testing of the radiation therapy devices. The processor is further configured to perform an analysis of a first QA data set obtained from a first one of the radiation therapy devices with respect to the compiled QA data.

In the sixth embodiments, or any other disclosed embodiment, the system further comprises the first one of the radiation therapy devices, which is a linear accelerator having a multi-leaf collimator (MLC).

In the sixth embodiments, or any other disclosed embodiment, the system further comprises a beam configuration module configured to calculate parameters for a selected dose calculation algorithm for the first one of the radiation therapy devices and to generate the first QA data set. In the sixth embodiments, or any other disclosed embodiment, the system further comprises a dose calculation server with a second memory configured to store data and/or parameters from the beam configuration module.

In the sixth embodiments, or any other disclosed embodiment, the system further comprises a network operatively connected to the QA data module, the first one of the radiation therapy devices, and/or another one of the radiation therapy devices. The network is configured to transmit data to/from connected devices and/or the module.

In the sixth embodiments, or any other disclosed embodiment, the system further comprises a controller of the first one of the radiation therapy devices. The controller is configured to automatically transmit the first QA data set to the QA data module.

In the sixth embodiments, or any other disclosed embodiment, the system further comprises a control panel configured such that an operator controls operation of the first one of the radiation therapy devices during the QA testing process.

In the sixth embodiments, or any other disclosed embodiment, the system further comprises one or more sensors disposed so as to detect irradiation beam data for the first QA data set during the QA testing process.

In the sixth embodiments, or any other disclosed embodiment, the system further comprises audio and/or visual indicators for communicating results of said analysis to an operator of the first one of the radiation therapy devices.

In the sixth embodiments, or any other embodiment, the system may be configured to perform the method (or parts thereof) of one or more of the fourth embodiments. It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The terms "system," "device," and "module" have been used interchangeably herein, and the use of one term in the description of an embodiment does not preclude the application of the other terms to that embodiment or any other embodiment.

It is thus apparent that there is provided, in accordance with the present disclosure, systems, methods, and devices for validation of commissioning and quality assurance data of a radiation therapy system. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A method for determining commissioning data of a first radiation therapy device, comprising:
   obtaining, at a commissioning device, a first data set from the first radiation therapy device undergoing a commissioning process, the first data set including irradiation beam data from the first radiation therapy device and corresponding system parameters;
   receiving, at the commissioning device, data from a plurality of already commissioned radiation therapy devices, said data being data obtained during respective commissioning of the plurality of radiation therapy devices, and including irradiation beam data from the plurality of radiation therapy devices and corresponding system parameters;
   compiling the data received from the plurality of radiation therapy devices so as to allow for a direct comparison between the compiled data and the first data set;
   performing an analysis of the first data set obtained from the first radiation therapy device with respect to predetermined limits and the compiled data;
   generating a notification signal based on a result of the analysis;
   determining an entity appropriate to receive the notification signal; and
   communicating the notification signal to the appropriate entity for further processing,
   wherein when the result of the analysis is that the first data set does not violate the predetermined limits and that a deviation from the compiled data is less than a predetermined threshold, the first data set is saved as the commissioning data for the first radiation therapy device and/or the first data set is sent to a dose calculation device for further processing.

2. The method of claim 1, wherein:
   when the result of the analysis is that the first data set violates the predetermined limits, an indication of an error is provided to a monitoring device of the first radiation therapy device,
   when the result of the analysis is that the first data set deviates from the compiled data by more than the predetermined threshold without violating the predetermined limits, an indication of a potential error is provided to the monitoring device of the first radiation therapy device.

3. The method of claim 1, wherein the irradiation beam data includes at least one of depth dose curves, dose profiles, output factor, and absolute point dose.

4. The method of claim 1, wherein the first data set is obtained by calculating parameters for a selected dose calculation algorithm for the first radiation therapy device.

5. The method of claim 1, wherein the compiling includes storing data in a common storage medium separate from at least one of the plurality of already commissioned radiation therapy devices.

6. The method of claim 1, further comprising measuring the first data set during the commissioning process of the first radiation therapy device.

7. The method of claim 2, wherein providing the indication of a potential error includes displaying a list of one or more potential causes for the deviation.

8. The method of claim 3, wherein the system parameters include at least one of field size, beam energy, sensor chamber type, source-surface distance (SSD), sensor depth, multi-leaf collimator (MLC) transmission factor, MLC dosimetric leaf gap (DLG), type of MLC, and type of dose calculation algorithm.

9. The method of claim 4, further comprising calculating dose for irradiation of a patient by the first radiation therapy device based on the calculated parameters and the first data set.

10. The method of claim 5, wherein when the result of the analysis is that the first data set does not violate predetermined limits and has a deviation from the compiled data less than the predetermined threshold, the first data set is saved in the common storage medium for periodic quality assurance and/or in a distributed dose calculation framework server for irradiation dose calculation.

11. The method of claim 6, further comprising, when the result of the analysis is that the first data set violates the predetermined limits, requiring measurement of a second data set for the first radiation therapy device and repeating the analysis on the second data set.

12. The method of claim 6, further comprising, when the result of the analysis is that the first data set deviates from the compiled data by more than the predetermined threshold without violating the predetermined limits:
   obtaining operator authorization to send the first data set to a dose calculation server for subsequent use in calculating dose for irradiation of a patient; or
   requiring measurement of a second data set for the first radiation therapy device and repeating the analysis on the second data set.

13. A system for determining commissioning data for a first radiation therapy device, comprising:
   a commissioning device comprising a processor and a first memory,
   wherein the processor is configured to:

receive a first data set from the first radiation therapy device undergoing a commissioning process;

receive data from a plurality of already commissioned radiation therapy devices, said data being obtained during respective commissioning of the plurality of radiation therapy devices;

compile the received data so as to allow for a direct comparison between the compiled data and the first data set;

perform an analysis of the first data set with respect to predetermined limits and the compiled data;

generate a notification signal based on a result of the analysis;

determine an entity appropriate to receive the notification signal; and communicate the notification signal to the appropriate entity for further processing, wherein when the result of the analysis is that the first data set does not violate the predetermined limits and that a deviation from the compiled data is less than a predetermined threshold, the first data set is saved as the commissioning data for the first radiation therapy device and/or the first data set is communicated to a dose calculation device for further processing.

14. The system of claim 13, further comprising the first radiation therapy device, wherein the first radiation therapy device is a linear accelerator having a multi-leaf collimator (MLC).

15. The system of claim 13, further comprising a beam configuration module configured to calculate parameters for a selected dose calculation algorithm for the first radiation therapy device and to generate the first data set.

16. The system of claim 13, wherein the processor is configured to:
when the result of the analysis is that the first data set violates predetermined limits, provide an indication of an error; and
when the result of the analysis is that the first data set deviates from the compiled data by more than the predetermined threshold without violating the predetermined limits, provide an indication of a potential error.

17. The system of claim 15, further comprising a dose calculation server with a second memory configured to store data and/or parameters from the beam configuration module.

18. The system of claim 15, further comprising:
a second memory for use by the first radiation therapy device and separate from the first memory,
wherein the processor is configured to send the first data set to the second memory for storage therein when the analysis indicates that the first data set is compliant or is otherwise approved by a user of the first radiation therapy device.

19. A non-transitory computer-readable storage medium upon which is embodied a sequence of programmed instructions for commissioning validation of a radiation therapy device, and a computer processing system that executes the sequence of programmed instructions embodied on the computer-readable storage medium to cause the computer processing system to:
receive a first data set from the first radiation therapy device undergoing a commissioning process;
receive data from a plurality of already commissioned radiation therapy devices, said data being obtained during respective commissioning of the plurality of radiation therapy devices;
compile the received data so as to allow for direct comparison between the compiled data and the first data set;
perform an analysis of the first data set with respect to predetermined limits and the compiled data;
generate a notification signal based on a result of the analysis;
determine an entity appropriate to receive the notification signal; and
communicate the notification signal to the appropriate entity for further processing,
wherein when the result of the analysis is that the first data set does not violate the predetermined limits and that a deviation from the compiled data is less than a predetermined threshold, the first data set is saved as commissioning data for the first radiation therapy device and/or the first data set is communicated to a dose calculation device for further processing.

20. The non-transitory computer-readable storage medium and computer processing system of claim 19, wherein the execution of the sequence of programmed instructions further causes the computer processing system to:
when the result of the analysis is that the first data set violates predetermined limits, provide an indication of an error that cannot be bypassed by an operator override, and
when the result of the analysis is that the first data set deviates from the compiled data by more than the redetermined threshold without violating the predetermined limits, provide an indication of a potential error that can be bypassed by the operator override.

21. The non-transitory computer-readable storage medium and computer processing system of claim 19, wherein the data comprises irradiation beam data from the plurality of radiation therapy devices and corresponding system parameters.

22. The non-transitory computer-readable storage medium and computer processing system of claim 19, wherein the compiling includes storing data in a common storage medium separate from at least one of the plurality of radiation therapy devices.

23. The non-transitory computer-readable storage medium and computer processing system of claim 19, wherein the compiled data includes a history of changes to the plurality of radiation therapy devices and/or the first radiation therapy devices and a name or ID of operators initiating the changes.

24. The non-transitory computer-readable storage medium and computer processing system of claim 19, wherein the execution of the sequence of programmed instructions further causes the computer processing system to analyze the first data set with respect to factory data of the first radiation therapy device and/or with related parameters of factory settings.

25. The non-transitory computer-readable storage medium and computer processing system of claim 19, wherein the execution of the sequence of programmed instructions further causes the computer processing system to, when the result of the analysis is that the first data set violates the predetermined limits, require measurement of a second data set for the first radiation therapy device and repeat the analysis on the second data set.

26. The non-transitory computer-readable storage medium and computer processing system of claim 19, wherein the execution of the sequence of programmed instructions further causes the computer processing system to, when the result of the analysis is that the first data set deviates from the compiled data by more than the predetermined threshold without violating the predetermined limits:
    obtain operator authorization to send the first data set to the dose calculation server for subsequent use in calculating dose for irradiation of a patient; or
    require measurement of a second data set for the first radiation therapy device and repeat the analysis on the second data set.

27. The non-transitory computer-readable storage medium and computer processing system of claim 19, wherein the execution of the sequence of programmed instructions further causes the computer processing system to, when the result of the analysis is that the first data set does not violate the predetermined limits and has a deviation from the compiled data less than the predetermined threshold, save the first data set in the common storage medium for periodic quality assurance and/or in the dose calculation server for dose calculation.

* * * * *